US008815576B2

(12) United States Patent
Beer

(10) Patent No.: US 8,815,576 B2
(45) Date of Patent: Aug. 26, 2014

(54) CHIP-BASED SEQUENCING NUCLEIC ACIDS

(75) Inventor: Neil Reginald Beer, Pleasanton, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 1604 days.

(21) Appl. No.: 11/965,585

(22) Filed: Dec. 27, 2007

(65) Prior Publication Data
US 2010/0184020 A1 Jul. 22, 2010

(51) Int. Cl.
C12Q 1/68 (2006.01)
C12M 1/00 (2006.01)
C12M 3/00 (2006.01)
C12M 1/34 (2006.01)

(52) U.S. Cl.
USPC ..... 435/287.2; 435/6.1; 435/6.12; 435/283.1; 435/287.1

(58) Field of Classification Search
USPC ............ 435/6, 6.1, 6.11, 283.1, 287.1, 287.2, 435/518
See application file for complete search history.

(56) References Cited

U.S. PATENT DOCUMENTS

| | | | | |
|---|---|---|---|---|
| 5,498,392 A * | 3/1996 | Wilding et al. | ............... | 422/68.1 |
| 5,604,097 A | 2/1997 | Brenner | | |
| 5,667,976 A * | 9/1997 | Van Ness et al. | ................. | 435/6 |
| 5,705,628 A | 1/1998 | Hawkins | | |
| 2002/0023909 A1* | 2/2002 | Usui | ............................. | 219/236 |
| 2002/0032242 A1 | 3/2002 | Antonietti et al. | | |
| 2002/0119482 A1* | 8/2002 | Nelson et al. | ..................... | 435/6 |
| 2002/0172969 A1 | 11/2002 | Burns et al. | | |
| 2003/0008285 A1 | 1/2003 | Fischer | | |
| 2003/0100102 A1 | 5/2003 | Rothberg et al. | | |
| 2003/0108867 A1 | 6/2003 | Chee et al. | | |
| 2004/0005720 A1* | 1/2004 | Cremer et al. | ................ | 436/518 |
| 2004/0086927 A1 | 5/2004 | Atwood et al. | | |
| 2004/0096960 A1 | 5/2004 | Burd Mehta et al. | | |
| 2004/0214175 A9 | 10/2004 | McKernan et al. | | |
| 2005/0042639 A1 | 2/2005 | Knapp et al. | | |
| 2005/0048581 A1 | 3/2005 | Chiu et al. | | |
| 2005/0072674 A1 | 4/2005 | Heins et al. | | |
| 2005/0136258 A1* | 6/2005 | Nie et al. | ...................... | 428/402 |
| 2005/0244870 A1 | 11/2005 | Chee et al. | | |
| 2005/0252773 A1 | 11/2005 | McBride et al. | | |
| 2005/0287572 A1* | 12/2005 | Mathies et al. | ................... | 435/6 |
| 2006/0019264 A1 | 1/2006 | Attiya et al. | | |
| 2006/0172408 A1 | 8/2006 | Quake et al. | | |
| 2007/0243634 A1* | 10/2007 | Pamula et al. | ................ | 436/518 |
| 2008/0014589 A1* | 1/2008 | Link et al. | ......................... | 435/6 |

FOREIGN PATENT DOCUMENTS

WO   WO 9960170 A1 * 11/1999 ............... C12Q 1/68

* cited by examiner

Primary Examiner — Robert T. Crow
(74) Attorney, Agent, or Firm — Eddie E. Scott

(57) ABSTRACT

A system for fast DNA sequencing by amplification of genetic material within microreactors, denaturing, demulsifying, and then sequencing the material, while retaining it in a PCR/sequencing zone by a magnetic field. One embodiment includes sequencing nucleic acids on a microchip that includes a microchannel flow channel in the microchip. The nucleic acids are isolated and hybridized to magnetic nanoparticles or to magnetic polystyrene-coated beads. Microreactor droplets are formed in the microchannel flow channel. The microreactor droplets containing the nucleic acids and the magnetic nanoparticles are retained in a magnetic trap in the microchannel flow channel and sequenced.

20 Claims, 10 Drawing Sheets

CHIP-BASED SEQUENCING NUCLEIC ACIDS

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to sequencing and more particularly to chip-based nucleic acid sequencing.

2. State of Technology

DNA sequencing has emerged as the mainstay of genetic medicine, forensics, genetic engineering, biological classification, epidemiology, and drug discovery. The available genomes to sequence are practically infinite and include: individual human genomes, animal, plant, bacteria, and viral genomes. Furthermore, low cost human genome sequencing is poised to usher in a revolution in personalized medicine, allowing drugs tailored to each individual's genetic composition. Genetic agriculture engineering, microbiology, zoology, and forensic science will add to the required sequencing capability. Additionally, the expanding knowledge of the viral genomes points to an ever-growing viral diversity, with new and unknown pathogens to sequence arising frequently. Since viral mutation rates occur quickly, they will always provide important sequencing targets. Individually these sequencing needs would swamp the current capacity based on current electrophoresis technologies. Taken in the aggregate, only a revolutionary, high-throughput, and inexpensive sequencing approach can address the critical sequencing need.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Microfluidic devices are poised to revolutionize environmental, chemical, biological, medical, and pharmaceutical detectors and diagnostics. "Microfluidic devices" loosely describes the new generation of instruments that mix, react, count, fractionate, detect, and characterize complex gaseous or liquid-solvated samples in a micro-optical-electro-mechanical system (MOEMS) circuit manufactured through standard semiconductor lithography techniques. These techniques allow mass production at low cost as compared to previous benchtop hardware. The applications for MOEMS devices are numerous, and as diverse as they are complex.

As sample volumes decrease, reagent costs plummet, reactions proceed faster and more efficiently, and device customization is more easily realized. By reducing the reaction volume, detection of target molecules occurs faster through improved sensor signal to noise ratio over large, cumbersome systems. However, current MOEMS fluidic systems may only be scratching the surface of their true performance limits as new techniques multiply their sensitivity by ten, a hundred, or even a thousand times.

The present invention provides a method of fast DNA sequencing by amplification of the genetic material within microreactors, denaturing and demulsifying and then sequencing the material, while retaining it in the PCR/Sequencing Zone by a magnetic field. The magnetic field holds the particles in place to permit washing away reaction products and excess reagents (and/or removing these by chemical degradation), and finally to ready the chamber for treatment of the next sample by turning off the magnetic field and permitting the entire content to be flushed to waste or archival storage.

The present invention provides a method of hybridizing individual single or double stranded nucleic acids to magnetic-cored optically discrete nanoparticles; isolating the nanoparticles within nanoliter to picoliter sized chemical reactors, amplifying the nucleic acids through PCR or isothermal amplification, trapping the nanoparticles in a magnetic field, sequencing them, and releasing them. This method allows for nucleic acid isolation to prevent cross contamination during PCR. It also provides a method for fixing the nanoparticles in a 2-D surface for time-dependent sequencing. The present invention also utilizes the novel magnetic nanoparticles that provide more than 1000 distinct spectral signatures to allow imaging of distinct particle location and tracking, solving the problem of particle overlay confusing the data collection. Additionally in one embodiment, the present invention employ magnetic-cored polystyrene beads in place of the novel nanoparticles, with the channel height fabricated low enough to eliminate particle overlay in the vertical dimension.

The present invention allows the detection and characterization of novel viruses and organisms by sequencing of previously unknown genetic material. Furthermore, the present invention allows for: reduction of costly reagent volumes, production of massively parallel and inexpensive microfluidic analysis chips, and scalable mass production of such chips.

In one embodiment, the present invention provides an apparatus for sequencing nucleic acids. The apparatus includes a microchip; a flow channel in the microchip; a source of carrier fluid connected to the flow channel; magnetic particles connected to the nucleic acids; a microreactor maker connected to the flow channel for producing microreactors containing the nucleic acids and the magnetic particles; a reagent source connected to the flow channel; a nucleotides source connected to said flow channel for introducing NTP1 nucleotides, NTP2 nucleotides, NTP3 nucleotides, and NTP4 nucleotides into said flow channel; a PCR and sequencing zone in the flow channel; an electromagnet trap for selectively magnetically trapping the nucleic acids and the magnetic particles in the PCR and sequencing zone in the flow channel; a thermalcycler connected to the PCR and the sequencing zone in the flow channel; and a detector for detection and sequencing of the nucleic acids.

In another embodiment, the present invention provides a method of sequencing nucleic acids on a microchip. The method includes the steps of providing a microchannel flow channel in the microchip; isolating the nucleic acids; hybridizing the nucleic acids to magnetic nanoparticles or to magnetic polystyrene-coated beads; forming microreactors in the microchannel flow channel, the microreactors containing the nucleic acids and the magnetic nanoparticles or magnetic polystyrene-coated beads; positioning the microreactor droplets containing the nucleic acids and the magnetic nanoparticles or magnetic polystyrene-coated beads in a magnetic trap in the microchannel flow channel, and sequencing the nucleic acids.

The present invention provides a system for enhancing a microfluidic detector's limits by magnetically focusing the target analytes to be detected in an optical convergence zone until interrogation has been performed. The present invention allows for a reduction of costly reagent volumes over standard MEMS systems, since much fewer targeted reactions are needed to produce a detectable signal. This not only provides the desirable cost incentive, but can cut processing times by an order of magnitude, making many popular on-chip process, such as Polymerase Chain Reaction (PCR) truly real time. The benefits to bacterial, viral, chemical, explosives, and other detection, as well as point-of-care diagnostics cannot be overstated.

The present invention also provides a system for performing sample wash steps in-line to cleanse the sample of unwanted reaction by-products, change the buffered pH, introduce new or next-step reagents, and remove excess or previous-step reagents from the reaction and detection zones. This opens the door to multi-step sequential reactions occurring while the target molecules or complexes are held within a detection and imaging zone.

Optical detection typically employs fluorescent probes which emit light when an electron which has been previously excited to an energy level above the ground state then gives off a photon to transition back to the ground state. For this process to occur in a solution, the pH of the solvent is critical as it affects the ability of the outer shell electrons in the probe molecule to efficiently transition between states. The present invention provides a system of magnetic focusing as the solvent stream buffer is changed which allows the real-time determination of the optimal buffer pH as well as the ability to run the reaction at one pH and the subsequent detection at another, thereby utilizing different pH's at each step so both can be optimized.

There are many uses for the present invention. For example, the invention has use in biomedical applications for: low-cost sequencing of individual human genomes; low-cost sequencing of animal, microbial, and viral genomes; detection of single nucleotide polymorphisms (SNP) for genetic medicine; identifying outbreaks of infectious disease including emerging, previously unidentified and genetically engineered pathogens; automated amplification, and detection of host or microbial and viral DNA or RNA in biological fluids for medical purposes; high throughput genetic screening for drug discovery and novel therapeutics; biowarfare detection applications; identifying bio-threat agents that contain nucleic acid signatures, such as spores, bacteria, viruses etc. The invention also has use in forensic applications including automated amplification, and detection DNA in biological fluids for forensic purposes.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1A:
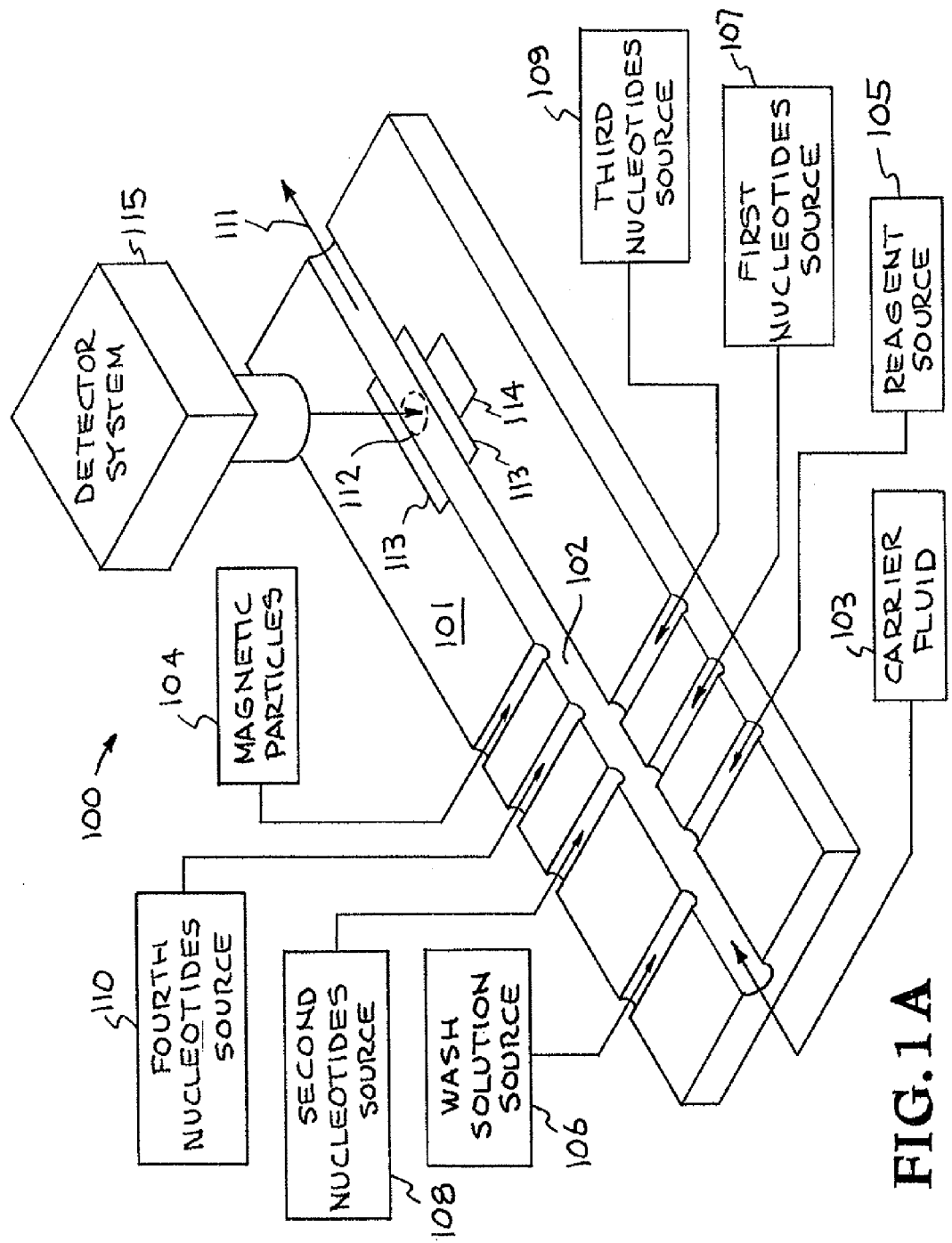
FIG. 1A illustrates one embodiment of a system for sequencing a nucleic acid constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1A, one embodiment of a system for sequencing a nucleic acid constructed in accordance with the present invention is illustrated. The system is designated generally by the reference numeral 100. The system 100 provides sequencing individual single or double stranded nucleic acids by isolating the nucleic acid, hybridizing the nucleic acid to magnetically-cored nanoparticles or to magnetic polystyrene-coated beads, amplifying the nucleic acids through PCR or isothermal amplification, positioning the nucleic acid in a magnetic trap, and sequencing the nucleic acid. The system 100 is capable of performing, singly or in combination, reagent and analyte mixing, cell-lysing, nucleic acid amplification, optical detection of amplification, reagent mixing for sequencing, optical detection of sequencing (which provides the exact sequence), and reagent wash to prevent cross contamination or reaction inhibition with the next analysis run.

The system 100 provides sequencing a nucleic acid on a microchip 101. The microchip 101 includes a microchannel flow channel 102. A carrier fluid source 103 introduces a carrier fluid into the flow channel 102. The sample to be analyzed together with suspended magnetic particles 104 is introduced to the flow channel 102 and droplets or microreactors containing the sample with magnetic particles 104 are formed. The flow channel 102 can carry genomic viral, bacterial, plant, animal, or human nucleic acid hybridized to magnetic-cored nanoparticles (or polystyrene beads). The microchannel flow channel 102 cross section aspect ratio, width and depth, is sized to prevent the sample and magnetic nanoparticles 104 (or magnetic polystyrene-coated beads) from vertical stacking.

A reagent source 105 introduces reagents into the flow channel 102. A wash solution source 106 allows a wash solution to be introduced into the flow channel 102 as needed. The flow channel 102 serves to mix various PCR components (i.e., genomic DNA or RNA template strand hybridized to the magnetic-cored nanoparticle or polystyrene bead, oligonucleotides, primer, probe, enzymes etc.) in preparation for amplification and detection.

Deoxyribonucleic acid (DNA) and ribonucleic acid (RNA) components are added to the flow channel 102. The four bases found in DNA are adenine (A), cytosine (C), guanine (G), and thymine (T). A nucleotides source (107-110) is connected to the flow channel 102 for introducing the DNA or RNA components into the flow channel 102. In the embodiment shown in FIG. 1A a first nucleotides (dNTP1) source 107 introduces dNTP1 nucleotides into the flow channel 102. A second nucleotides (dNTP2) source 108 introduces dNTP2 nucleotides into the flow channel 102. A third nucleotides (dNTP3) source 109 introduces dNTP3 nucleotides into the flow channel 102. A fourth nucleotides (dNTP4) source 110 introduces dNTP4 nucleotides into the flow channel 102. It is understood that one source can be used to introduce the nucleotides into the flow channel 102.

The droplets or microreactors (or a PCR emulsion device with two-phase flow or separated into liquid slugs metered by air) containing the sample with magnetic particles 104 are carried to a PCR/sequencing zone 112 by the carrier fluid. The droplets or microreactors containing the sample with magnetic particles 104 are trapped in the PCR/sequencing zone 112 by activation of electromagnets 113. The drops (isolated mobile PCR reactors) with their suspended magnetic particles are captured in the magnetic and fluidic trap (PCR/sequencing zone) 112 using the electro magnets 113. A thermalcycler 114 provides PCR and/or sequencing of the sample. A detector system 115 provides detection and sequencing of the sample.

The reactions between the hybridized molecules on the magnetic nanoparticle and the catalyzed and buffered reagents within the aqueous stream occur, powered by the addition of heat or light into the channel if necessary. When the droplets pass through the optical enhancement, or "Capture Zone" 112, the electromagnets 113 strip the passing droplets of their nanoparticles. The detector system 115 provides sequencing of the nucleic acids. As the entire channel begins to fill, optical density reaches a practical maximum, and the nanoparticles are excited by laser or LED light source into fluorescence. As they fluoresce, their emission is read by a photodiode with amplification (such as a Trans-impedance amplifier), or an imaging system such as a CCD or CMOS array. After the measurement is taken, the magnets are de-energized and the magnetic beads, or nanoparticles, wash away as illustrated at 111, clearing the channel 102 for the next assay.

Alternate embodiments utilize the same system applied to aqueous flows under Poiseiulle (parabolic) profiles, electrophoretic flows, segmented slug flows (aqueous with gas pockets), and others. Each requires simply a tuning of the magnetic force applied to capture and hold the magnetic nanoparticles. The system 100 employs detection focusing to concentrate all available optical (fluorescent) reporters within the detection zone, instead of the accepted method of detect-as-you-flow which provides a much lower fluorophore concentration. In the system 100, flow occurs in the detector channel 102, whether it is continuous flow, such as in a capillary electrophoresis or flow cytometry device, or discrete segmented flow, such as in a PCR emulsion device with two-phase flow, or separated into liquid slugs metered by air, oil, or other immiscible liquid (i.e. Fluorinert fluorocarbon-based fluid), as many current MOEMS chemical/biological detectors are. These devices contain radically different physical processes regarding their flow velocity profile (Poiseiulle or slug), surface tension (two-phase and emulsions), and presence or absence of electrical and ionic gradients that drive or hinder the target's flow. However at the heart of their operation, all of these devices must detect the signal, MOEMS devices use an optical excitation and a wavelength shifted emission, typically of a molecular "reporter" that binds to the target molecule, nucleic acid, or chemical complex to be detected, characterized, counted, or modified.

Referring again to FIG. 1A, sample washing and reagent replacement or refresh can also be performed with this system 100. The target molecules, attached to the magnetic beads and held in the detection zone, can be washed by the continuous flow of the channel 102 which, with upstream valving, can bring new and different reagents for multi-step reactions, or change the buffered pH to improve the optical efficiency of the fluorescing probe. For reagent sequencing, this method allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" by electromagnetic attraction. It should be noted that fluorescence requires an excitation source to raise electrons to their excited state.

The system 100 can perform in-line sample focusing of target analytes, whether in continuous flow, slug flow, or partitioned in emulsion microreactors, for subsequent optical detection at greatly reduced times compared to other methods. The system 100 can also perform in-line sample washing and buffering for complex reactions, and a real-time system for enhancing fluorescence detection through pH optimization.

Figure 1B:
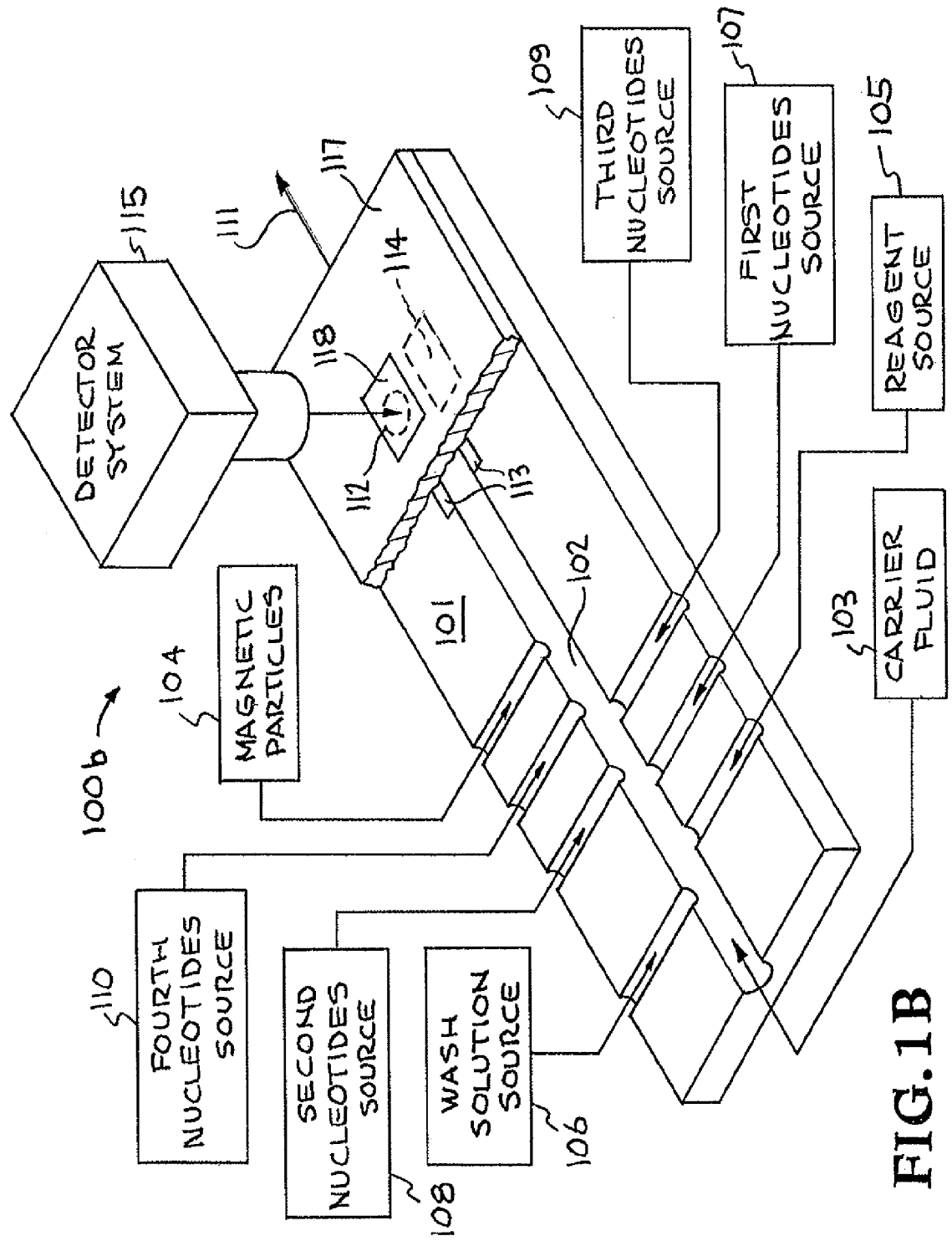
FIG. 1B illustrates another embodiment of a system for sequencing a nucleic acid constructed in accordance with the present invention.

Referring now to FIG. 1B, another embodiment of a system for sequencing a nucleic acid constructed in accordance with the present invention is illustrated. The FIG. 1B system is designated generally by the reference numeral 100*b*. The 100*b* system is substantially similar to the system 100 illustrated in FIG. 1A. Accordingly, like reference numerals are used for like elements in the descriptions of FIG. 1A and FIG. 1B. The FIG. 1B system 100*b* differs from the FIG. 1A system 100 in that a cover 117 with appropriate diagnostic window(s) 118 is positioned over the microchip 101.

The system 100*b* provides sequencing a nucleic acid on a microchip 101. A cover 117 with appropriate diagnostic window(s) 118 is positioned over the microchip 101. The microchip 101 includes a microchannel flow channel 102. A carrier fluid source 103 introduces a carrier fluid into the flow channel 102. The sample to be analyzed together with suspended magnetic particles 104 is introduced to the flow channel 102 and droplets or microreactors containing the sample with magnetic particles 104 are formed. The flow channel 102 can carry genomic viral, bacterial, plant, animal, or human nucleic acid hybridized to magnetic-cored nanoparticles (or polystyrene beads). The microchannel flow channel 102 cross section aspect ratio, width and depth, is sized to prevent the sample and magnetic nanoparticles 104 (or magnetic polystyrene-coated beads) from vertical stacking.

A reagent source 105 introduces reagents into the flow channel 102. A wash solution source 106 allows a wash solution to be introduced into the flow channel 102 as needed. The flow channel 102 serves to mix various PCR components (i.e., genomic DNA or RNA template strand hybridized to the magnetic-cored nanoparticle or polystyrene bead, oligonucleotides, primer, probe, enzymes etc.) in preparation for amplification and detection.

Deoxyribonucleic acid (DNA) and ribonucleic acid (RNA) components are added to the flow channel 102. The four bases found in DNA are adenine (A), cytosine (C), guanine (G), and thymine (T). A nucleotides source (107-110) is connected to the flow channel 102 for introducing the DNA or RNA components into the flow channel 102. In the embodiment shown in FIG. 1B a first nucleotides (dNTP1) source 107 introduces dNTP1 nucleotides into the flow channel 102. A second nucleotides (dNTP2) source 108 introduces dNTP2 nucleotides into the flow channel 102. A third nucleotides (dNTP3) source 109 introduces dNTP3 nucleotides into the flow channel 102. A fourth nucleotides (dNTP4) source 110 introduces dNTP4 nucleotides into the flow channel 102. It is understood that one source can be used to introduce the nucleotides into the flow channel 102.

The droplets or microreactors (or a PCR emulsion device with two-phase flow or separated into liquid slugs metered by air) containing the sample with magnetic particles 104 are carried to a PCR/sequencing zone 112 by the carrier fluid. The droplets or microreactors containing the sample with magnetic particles 104 are trapped in the PCR/sequencing zone 112 by activation of electromagnets 113. The drops (isolated mobile PCR reactors) with their suspended magnetic particles are captured in the magnetic and fluidic trap (PCR/sequencing zone) 112 using the electro magnets 113. A thermalcycler 114 provides PCR and/or sequencing of the sample. A detector system 115 provides detection and sequencing of the sample.

The reactions between the hybridized molecules on the magnetic nanoparticle and the catalyzed and buffered reagents within the aqueous stream occur, powered by the addition of heat or light into the channel if necessary. When the droplets pass through the optical enhancement, or "Capture Zone" 112, the electromagnets 113 strip the passing droplets of their nanoparticles. The detector system 115 provides sequencing of the nucleic acids. As the entire channel begins to fill, optical density reaches a practical maximum, and the nanoparticles are excited by laser or LED light source into fluorescence. As they fluoresce, their emission is read by a photodiode with amplification (such as a Trans-impedance amplifier), or an imaging system such as a CCD or CMOS array. After the measurement is taken, the magnets are de-energized and the magnetic beads, or nanoparticles, wash away as illustrated at 111, clearing the channel 102 for the next assay.

The system 100b provides sequencing individual single or double stranded nucleic acids by isolating the nucleic acid, hybridizing the nucleic acid to magnetically-cored nanoparticles or to magnetic polystyrene-coated beads, amplifying the nucleic acids through PCR or isothermal amplification, positioning the nucleic acid in a magnetic trap, and sequencing the nucleic acid. The system 100b is capable of performing, singly or in combination, reagent and analyte mixing, cell-lysing, nucleic acid amplification, optical detection of amplification, reagent mixing for sequencing, optical detection of sequencing (which provides the exact sequence), and reagent wash to prevent cross contamination or reaction inhibition with the next analysis run.

Referring again to FIG. 1B, sample washing and reagent replacement or refresh can also be performed with this system 100b. The target molecules, attached to the magnetic beads and held in the detection zone, can be washed by the continuous flow of the channel 102 which, with upstream valving, can bring new and different reagents for multi-step reactions, or change the buffered pH to improve the optical efficiency of the fluorescing probe. For reagent sequencing, this method allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" by electromagnetic attraction. It should be noted that fluorescence requires an excitation source to raise electrons to their excited state.

The system 100b can perform in-line sample focusing of target analytes, whether in continuous flow, slug flow, or partitioned in emulsion microreactors, for subsequent optical detection at greatly reduced times compared to other methods. The system 100b can also perform in-line sample washing and buffering for complex reactions, and a real-time system for enhancing fluorescence detection through pH optimization.

Figure 2A:
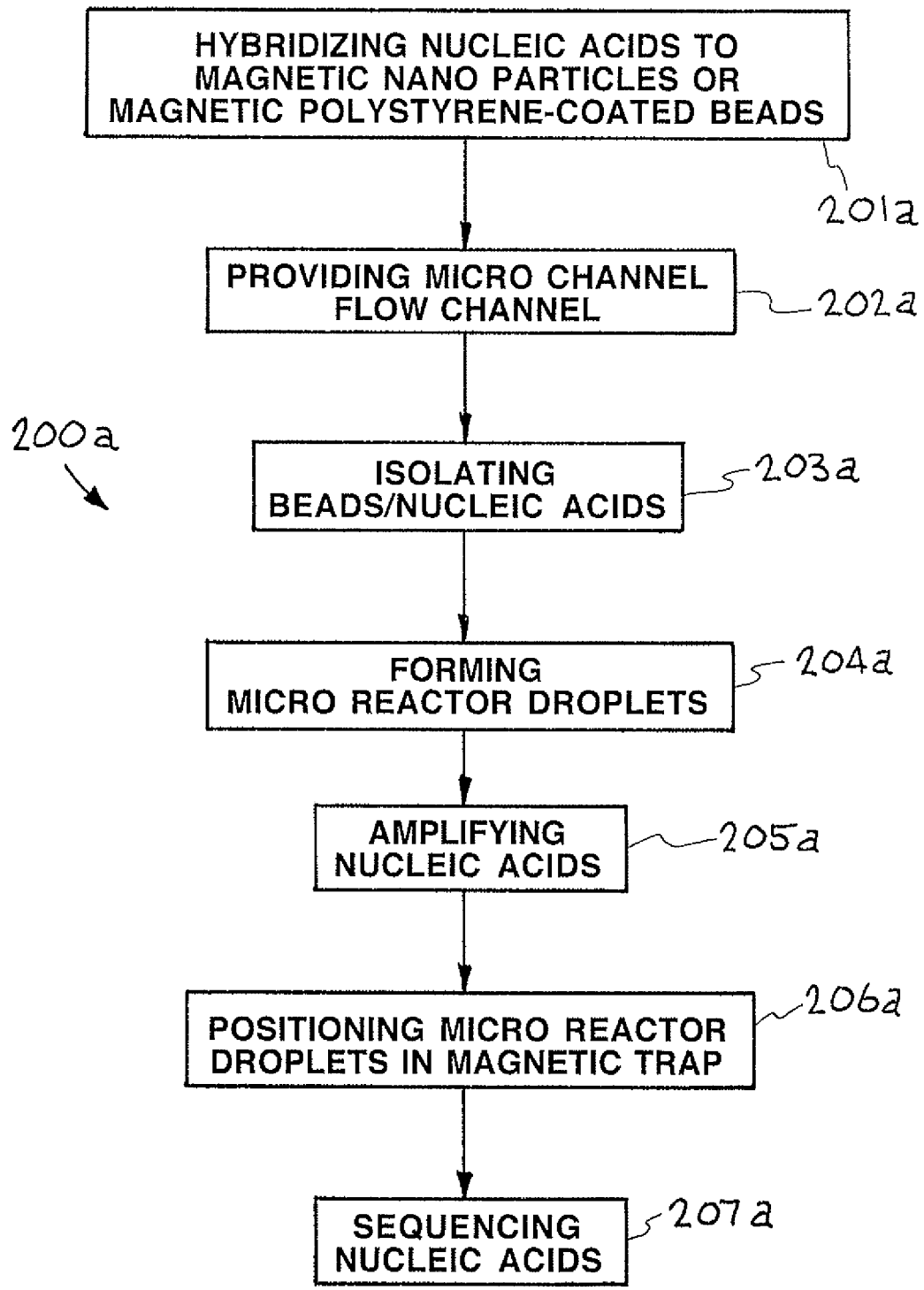
FIGS. 2A and 2B illustrate embodiments of methods of sequencing nucleic acids on a microchip.

Referring now to FIG. 2A, one embodiment of a method of sequencing nucleic acids on a microchip is illustrated. The method is designated generally by the reference numeral 200a. The system 200a provides sequencing individual single or double stranded nucleic acids by isolating the nucleic acid, hybridizing the nucleic acid to magnetically-cored nanoparticles or to magnetic polystyrene-coated beads, positioning the nucleic acid in a magnetic trap, and sequencing the nucleic acid. The system 200a is capable of performing, singly or in combination, reagent and analyte mixing, cell-lysing, nucleic acid amplification, optical detection of amplification, reagent mixing for 4-color sequencing, optical detection of sequencing (which provides the exact sequence), and reagent wash to prevent cross contamination with the next analysis run.

As illustrated in FIG. 2A, the method 200a includes the step 201a of hybridizing the nucleic acids to magnetic nanoparticles or to magnetic polystyrene-coated beads, the step 202a of providing a microchannel flow channel in the microchip; the step 203a of isolating the nucleic acids; the step 204a of forming microreactor droplets in the microchannel flow channel, the microreactor droplets containing the nucleic acids and the magnetic nanoparticles or magnetic polystyrene-coated beads; the step 205a of amplifying the nucleic acids; the step 206a of positioning the microreactor droplets containing the nucleic acids and the magnetic nanoparticles or magnetic polystyrene-coated beads in a magnetic trap in the microchannel flow channel; and the step 207a of sequencing the nucleic acids.

Figure 2B:
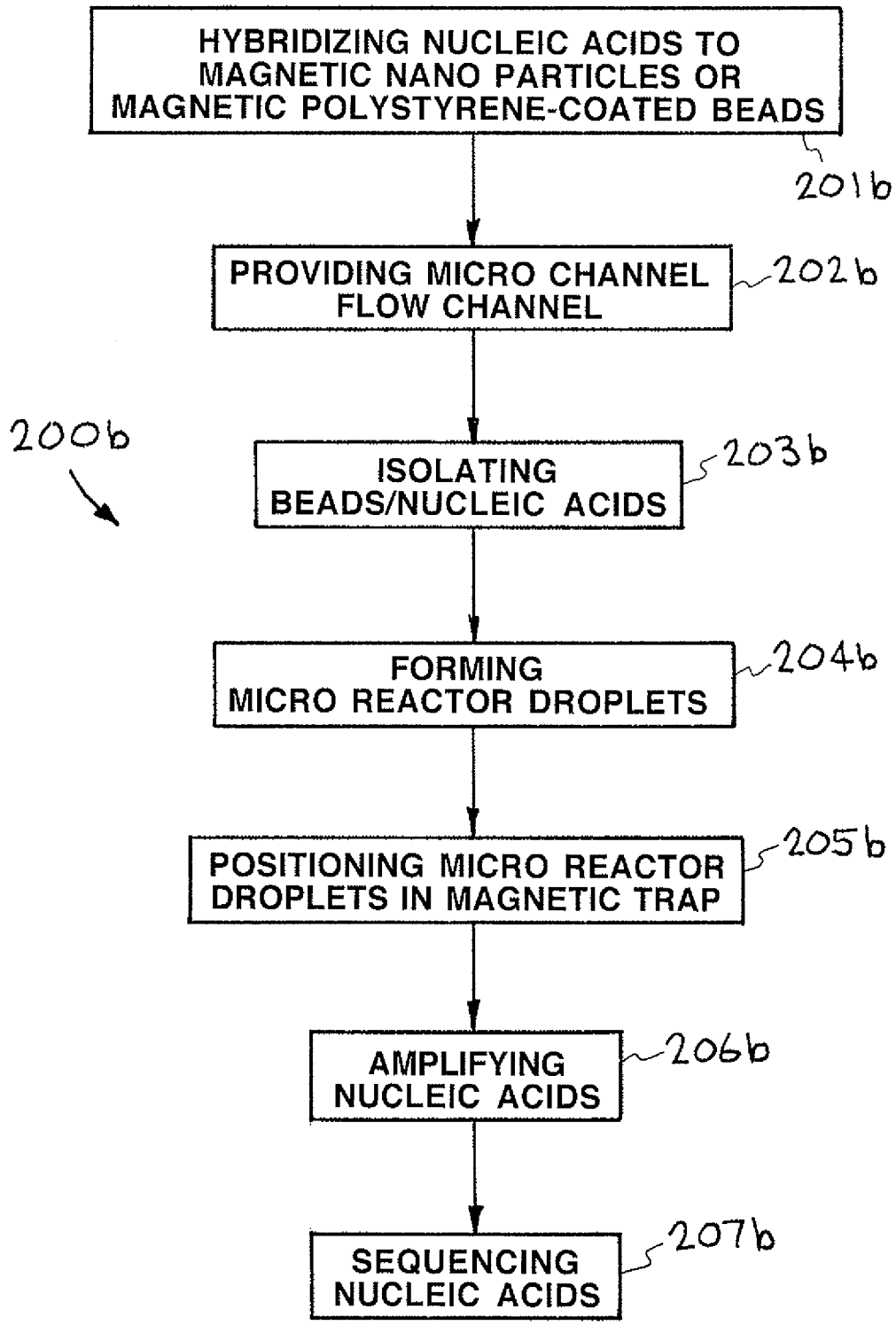

Referring now to FIG. 2B, another embodiment of a method of sequencing nucleic acids on a microchip is illustrated. The method is designated generally by the reference numeral 200b. The system 200b provides sequencing individual single or double stranded nucleic acids by isolating the nucleic acid, hybridizing the nucleic acid to magnetically-cored nanoparticles or to magnetic polystyrene-coated beads, positioning the nucleic acid in a magnetic trap, and sequencing the nucleic acid. The system 200b is capable of performing, singly or in combination, reagent and analyte mixing, cell-lysing, nucleic acid amplification, optical detection of amplification, reagent mixing for 4-color sequencing, optical detection of sequencing (which provides the exact sequence), and reagent wash to prevent cross contamination with the next analysis run.

As illustrated in FIG. 2B, the method 200b includes the step 201b of hybridizing the nucleic acids to magnetic nanoparticles or to magnetic polystyrene-coated beads, the step 202b of providing a microchannel flow channel in the microchip; the step 203b of isolating the nucleic acids; the step 204b of forming microreactor droplets in the microchannel flow channel, the microreactor droplets containing the nucleic acids and the magnetic nanoparticles or magnetic polystyrene-coated beads; the step 205b of positioning the microreactor droplets containing the nucleic acids and the magnetic nanoparticles or magnetic polystyrene-coated beads in a magnetic trap in the microchannel flow channel; the step 206b of amplifying the nucleic acids; and the step 207b of sequencing the nucleic acids.

The systems 200a and 200b employ magnetic beads or iron-cored nanoparticles coated with polystyrene. The magnetic beads have the ability to be coated, hybridized to, washed and removed in chemical reactions, to be captured within the optical focus, after the desired chemical reactions have occurred, within the microscale width of a MOEMS channel.

The magnetic nanoparticles are mixed with a nucleic acid sample and reagents and are formed into droplets by a droplet maker. The droplets flow through the systems 200a and 200b. The particles are coated through simple chemistry, with molecules that will bind with the chemical or biological molecule or complex that you wish to detect. The systems 200a and 200b pass the flow between electromagnets positioned above and below or on both sides of the channel to capture and highly concentrate the target molecules from the emulsion droplets, fluid slugs, or diluted stream. Whitesides et al. give the force developed in a magnetic trap by:

$$F = \frac{(\chi_p - \chi_m)V}{\mu_0}(B \cdot \nabla B)$$ [Equation 1]

Where V is the particle volume, $\mu_0$ is the magnetic permeability of free space, B is the magnetic field vector, and $(\chi_p - \chi_m)$ is the difference in the volumetric magnetic susceptibilities between the particle and the medium—in this case the flow medium (water, oil, gas, etc.)

To capture a particle and retain it in the optical intensity enhancement trap requires at a minimum the magnetic force overcoming the fluid drag force, which at the length scales of MOEMS circuits is governed by Stoke's flow. (Stoke's flow is a linearized solution of the Navier-Stokes equations which accounts for the insignificance of inertia affects to flow in micron-scale channels.)

$$F = 6\pi\mu U_0 a$$ [Equation 2]

Where $\mu$ is the fluid media viscosity, $U_0$ is the mean flow rate, and a is the particle radius. For emulsions, this assumes an upstream microdroplet generator (droplet maker) has been employed, such as the T-junction or flow focusing orifice, to create microdroplet reactors (aqeous droplets in an oil carrier flow or oil droplets in an aqeous flow) that are partitioned from each other and the fluid medium by the oil/water interface. The droplet maker is connected to the sample channel and the flow channel and produces droplets containing the sample and the magnetic particles. The droplet maker can be a "T" junction or other type of droplet maker. A droplet make is disclosed in the article, "Monodispersed microfluidic droplet generation by shear focusing microfluidic device," by Yung-Chieh Tan, Vittorio Cristini and Abraham P. Lee, in *Sensors and Actuators B: Chemical*, Volume 114, Issue 1, 30 Mar. 2006, Pages 350-35. The article, "Monodispersed microfluidic droplet generation by shear focusing microfluidic device," by Yung-Chieh Tan, Vittorio Cristini and Abraham P. Lee, in *Sensors and Actuators B: Chemical*, Volume 114, Issue 1, 30 Mar. 2006, Pages 350-35 is incorporated herein by reference.

This provides a method to retain the target molecules (analytes) within the magnetic trap for optical signal intensification even after the droplet which solvated the magnetic nanoparticles has passed from the zone. By employing enough magnetic field strength and adequately sized magnetic cores, the nanoparticles will be retained and will accumulate as droplet after droplet pass by and wash over them, releasing their nanoparticles into a growing fluorescent "cloud" at the optical detector.

In this magnetic emulsion particle capture system 200 the magnetic force will overcome both the Stoke's drag and the surface tension of the oil/water interface since the particles will pass though that interface. This effect, correctly applied, will provide the capability to increase the signal to noise or improve the instrument's limit of detection (LOD) proportional to the number of droplets that pass through the magnetic capture zone for optical interrogation. In this way 1000 droplets (approximately 1 second of droplet production for the author's microfluidic circuits) will increase the optical signal 3 orders of magnitude over any individual droplet. This effect will be useful in instruments that perform PCR, binding assays, chemical detection, and any other systems where near real-time performance or highly sensitive limits of detection are beneficial. This performance enhancement may provide the transformational impetus needed to move many biomedical instruments from the laboratory to point-of-care locations, and hence multiply the number of instruments needed. Similarly, the present invention will increase sensitivity and performance in slug flow systems (PCR by Quake and Thorsen) and continuous, non-segmented streams such as water quality monitoring MOEMS applications now becoming ubiquitous.

The systems 200a and 200b provide methods to uniquely deal with the radically different physics of the potential flow regimes at the microscale. For target molecule accumulation within the optical enhancement zone of a continuous flow partitioned (emulsion) system, the magnetic force will be increased (by increasing B) to not only counter Stoke's drag, but also to counter the significant resistance of breaking the magnetic nanoparticles through the surface tension at the water/oil interface. Of considerable benefit is that oil, a non-polar and non-magnetic fluid, has a much lower volumetric magnetic susceptibility than does water, a polar solvent. For other flow regimes, slug, or continuous with only aqueous contents, a lower magnetic force will suffice. No matter which flow regime is being employed, the method allows for the electromagnet to be de-energized, allowing all captive particles to wash downstream. The empty droplets are discarded, freeing the channel for the next experiment or measurement.

The captured magnetic particles are retained in a PCR zone and PCR is powered by cyclic heating and cooling. The reactions between the hybridized molecules on the magnetic nanoparticle and the catalyzed and buffered reagents within the aqueous stream occur, powered by the addition of heat or light into the channel if necessary. When the droplets pass through the optical enhancement, or "Capture Zone," the electromagnets strip the passing droplets of their nanoparticles, accumulating them first near the walls (close to the magnets) and then further and further into the free stream of the fluid flow.

The flow channel, in addition to thermal control and detection elements, contains optical windows for delivering and detecting light. As amplification occurs, detection of fluorescence-labeled TaqMan type, or other fluorescent probes occurs if desired. Following amplification the emulsions are broken, sequencing occurs as described above, and the dNTP's and sequencing reagents are sequentially washed over the captive particles. The imaging detector records particle location and intensity through each step of the process.

As the entire channel begins to fill, optical density reaches a practical maximum, and the nanoparticles are excited by laser or LED light source into fluorescence. As they fluoresce, their emission is read by a photodiode with amplification (such as a Trans-impedance amplifier), or an imaging system such as a CCD or CMOS array. After the measurement is taken, the magnets are de-energized and the magnetic beads, or nanoparticles, wash away, clearing the channel for the next assay. Once complete the magnets are de-energized and the particles washed out to waste. Priming the channel with an aqueous wash refreshes it for the next sequencing experiment.

Referring again to FIGS. 2A and 2B, sample washing and reagent replacement or refresh can also be performed with the systems 200a and 200b. The target molecules, attached to the magnetic beads and held in the detection zone, can be washed by the continuous flow of the channel which, with upstream valving, can bring new and different reagents for multi-step reactions, or change the buffered pH to improve the optical efficiency of the fluorescing probe. For reagent sequencing, this method allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" by electromagnetic attraction. It should be noted that fluorescence requires an excitation source to raise electrons to their excited state.

The systems 200a and 200b provide systems for up to a thousand fold signal enhancement for optical detection of bacterial cells, virus particles, nucleic acids, proteins, biomolecules, chemical agents, explosives agents, and other targets of interest in a microfluidic (MOEMS) device. The systems 200a and 200b can perform in-line sample focusing of target analytes, whether in continuous flow, slug flow, or partitioned in emulsion microreactors, for subsequent optical detection at greatly reduced times compared to other methods. The systems 200a and 200b can also perform in-line sample washing and buffering for complex reactions, and a real-time system for enhancing fluorescence detection through pH optimization.

Figure 3:
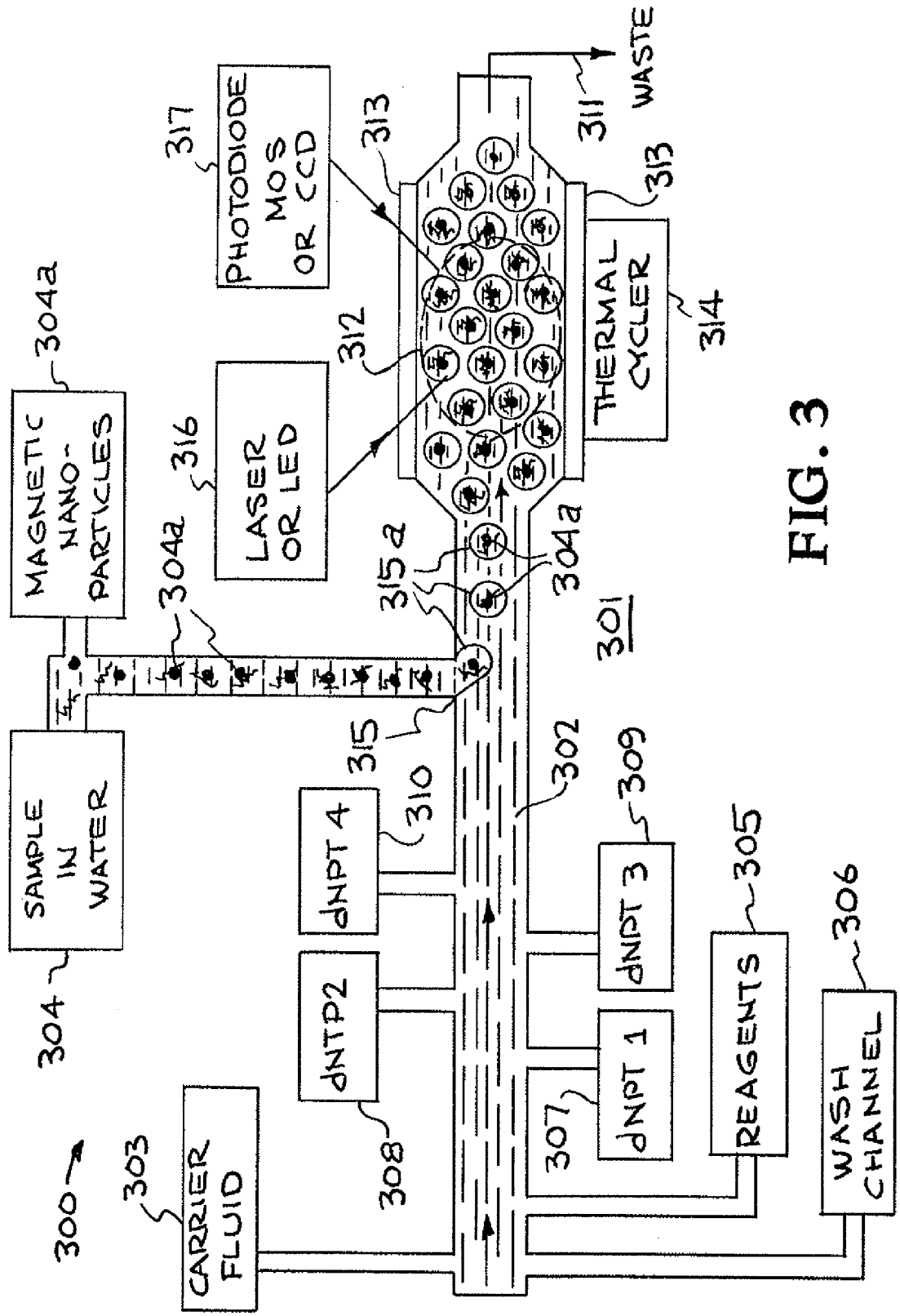
FIG. 3 illustrates another embodiment of a system for sequence analysis of a nucleic acid constructed in accordance with the present invention.

Referring now to FIG. 3, another embodiment of a system for analysis of a nucleic acid constructed in accordance with the present invention is illustrated. The system is designated generally by the reference numeral 300. The system 300 provides analysis of a nucleic acid by isolating the nucleic acid, hybridizing the nucleic acid to magnetically-cored nanoparticles or to magnetic polystyrene-coated beads, positioning the nucleic acid in a magnetic trap, and sequencing the nucleic acid.

The system 300 provides sequencing a nucleic acid on a microchip 301. The microchip 301 includes a microchannel flow channel 302. The microchannel flow channel cross section aspect ratio, width and depth, is sized to prevent the magnetic nanoparticles or magnetic polystyrene-coated beads from vertical stacking. A carrier fluid source 303 introduces a carrier fluid into the flow channel 302. The sample to be analyzed together with suspended magnetic particles 304a is introduced to the flow channel 302 and droplets or microreactors containing the sample with magnetic particles 304a are formed. The flow channel 302 can carry genomic viral, bacterial, plant, animal, or human nucleic acid hybridized to magnetic-cored nanoparticles (or polystyrene beads).

A reagent source 305 introduces reagents into the flow channel 302. A wash solution source 306 allows a wash solution to be introduced into the flow channel 302 as needed. Deoxyribonucleic acid (DNA) and ribonucleic acid (RNA) components are added to the flow channel 302. The four bases found in DNA are adenine (A), cytosine (C), guanine (G), and thymine (T). A first nucleotide (dNTP1) source 307 introduces dNTP1 nucleotides into the flow channel 302. A second nucleotide (dNTP2) source 308 introduces dNTP2 nucleotides into the flow channel 302. A third nucleotide (dNTP3) source 309 introduces dNTP3 nucleotides into the flow channel 302. A fourth nucleotide (dNTP4) source 310 introduces dNTP4 nucleotides into the flow channel 302.

A droplet maker 315 at the junction of the flow channel 302 and the sample to be analyzed together with suspended magnetic particles 304a microchannel produces droplets or microreactors 315a. The droplets or microreactors 315a containing the sample 304 with magnetic particles 304a are carried to a PCR/sequencing zone 312 by the carrier fluid. The droplets or microreactors 315a containing the sample 304 with magnetic particles 304a are trapped in the PCR/sequencing zone 312 by activation of electromagnets 313. The drops (isolated mobile PCR reactors) 315a with their suspended magnetic particles are captured in the magnetic and fluidic trap (PCR/sequencing zone) 312 using the electro magnets 313. A thermalcycler 314 provides PCR and/or sequencing of the sample. A detector system provides detection and sequencing of the sample.

The System 300

The system 300 provides a system for up to a thousand fold signal enhancement for optical detection of bacterial cells, virus particles, nucleic acids, proteins, biomolecules, chemical agents, explosives agents, and other targets of interest in a microfluidic (MOEMS) device. The system 300 can perform in-line sample focusing of target analytes, whether in continuous flow, slug flow, or partitioned in emulsion microreactors, for subsequent optical detection at greatly reduced times compared to other methods. The system 300 can also perform in-line sample washing and buffering for complex reactions, and a real-time system for enhancing fluorescence detection through pH optimization.

As illustrated in FIG. 3, an aqueous sample fluid 304 and magnetic nanoparticles 304a are injected into a cross-channel flow of carrier fluid 303. This can be accomplished by the carrier fluid 303 being drawn into a pressure driven hydraulic or pneumatic pump and then used to prime the mixing reactor 315 and flow path 302. The flow line 302 carries genomic viral, bacterial, plant, animal, or human nucleic acid hybridized to magnetic-cored nanoparticles (or polystyrene beads) along with the necessary PCR reagents. Sequencing reagents 305, 307, 308, 309, and 310 that are primed by sequentially drawing up fluid from individual reservoirs using pumps. The fluids are injected into the flow channel 302, generating isolated mobile PCR reactors.

The drops (isolated mobile PCR reactors) 315a with their suspended sample 304 and magnetic particles 304a are captured in the magnetic and fluidic trap 312 using magnets 313. The captured sample 304 and magnetic particles 304a are retained in a PCR zone 312 and PCR 314 is powered by cyclic heating and cooling. The flow channel 302, in addition to thermal control and detection elements, contains optical windows for delivering and detecting light. As amplification occurs, detection of fluorescence-labeled TaqMan type probes occurs if desired. Following amplification the emulsions are broken, sequencing or 4-color sequencing by synthesis occurs as described above, and the dNTP's and sequencing reagents are sequentially washed over the captive particles. The imaging detector records particle location and intensity through each step of the process. Once complete the magnets 313 are de-energized and the particles washed out to waste 311. Priming the channel 302 with an aqueous wash refreshes it for the next sequencing experiment.

Capture Zone 312

The reactions between the hybridized molecules on the magnetic nanoparticle 304a and the catalyzed and buffered reagents 305 within the aqueous stream occur, powered by the addition of heat or light into the channel if necessary. When the droplets pass through the optical enhancement, or "Capture Zone" 312, the electromagnets 313 strip the passing droplets of their nanoparticles, accumulating them first near the walls (close to the magnets) and then further and further into the free stream of the fluid flow. As the entire channel begins to fill, optical density reaches a practical maximum, and the nanoparticles are excited by laser or LED light source 316 into fluorescence. As they fluoresce, their emission is read by a photodiode with amplification (such as a Transimpedance amplifier), or an imaging system such as a CCD or CMOS array 317. After the measurement is taken, the magnets 313 are de-energized and the magnetic beads, or nanoparticles 304a, wash away, clearing the channel 302 for the next assay.

Alternate Embodiments

Alternate embodiments utilize the same method applied to aqueous flows under Poiseiulle (parabolic) profiles, electrophoretic flows, segmented slug flows (aqueous with gas pockets), and others. Each requires simply a tuning of the magnetic force applied to capture and hold the magnetic nanoparticles.

The system 300 employs detection focusing to concentrate all available optical (fluorescent) reporters within the detection zone, instead of the accepted method of detect-as-you-flow which provides a much lower fluorophore concentration. In the system 300, flow occurs in the detector channel 302, whether it is continuous flow, such as in a capillary electrophoresis or flow cytometry device, or discrete segmented flow, such as in a PCR emulsion device with two-phase flow, or separated into liquid slugs metered by air, as many current MOEMS chemical/biological detectors are. These devices contain radically different physical processes regarding their flow velocity profile (Poiseiulle or slug), surface tension (two-phase and emulsions), and presence or absence of electrical and ionic gradients that drive or hinder the target's flow. However at the heart of their operation, all of these devices must detect the signal, MOEMS devices use an optical excitation and a wavelength shifted emission, typically of a molecular "reporter" that binds to the target molecule, nucleic acid, or chemical complex to be detected, characterized, counted, or modified.

Operation of the System 300

The system 300 employs magnetic beads 304a (iron-cored nanoparticles coated with polystyrene), already common in the literature and market place for their ability to be coated, hybridized to, washed and removed in chemical reactions, to be captured within the optical focus, after the desired chemical reactions have occurred, within the microscale width of the typical MOEMS channel.

The magnetic nanoparticles 304a are mixed with the sample 304 and reagents 305 and PCR reagents 307, 308, 309, and 310 and are formed into droplets by a T-Junction droplet maker 315. The droplets flow through the device 300. The sample 304 and particles 304a are coated through simple chemistry, with molecules that will bind with the chemical or biological molecule or complex that you wish to detect. The system 300 passes the flow between two electromagnets 313 positioned above and below or on both sides of the channel 302 to capture and highly concentrate the target molecules from the emulsion droplets, fluid slugs, or diluted stream. Whitesides et al. give the force developed in a magnetic trap by:

$$F = \frac{(\chi_p - \chi_m)V}{\mu_0}(B \cdot \nabla B) \qquad \text{[Equation 1]}$$

Where V is the particle volume, $\mu_0$ to is the magnetic permeability of free space, B is the magnetic field vector, and $(\chi_p\text{-}\chi_m)$ is the difference in the volumetric magnetic susceptibilities between the particle and the medium—in this case the flow medium (water, oil, gas, etc.)

To capture a particle and retain it in the optical intensity enhancement trap requires at a minimum the magnetic force overcoming the fluid drag force, which at the length scales of MOEMS circuits is governed by Stoke's flow. (Stoke's flow is a linearized solution of the Navier-Stokes equations which accounts for the insignificance of inertia affects to flow in micron-scale channels.)

$$F = 6\pi\mu U_0 a \qquad \text{[Equation 2]}$$

Where $\mu$ is the fluid media viscosity, $U_0$ is the mean flow rate, and a is the particle radius. For emulsions, this assumes an upstream microdroplet generator has been employed, such as the T-junction or constricted orifice, to create microdroplet reactors 315a (aqueous droplets in an oil carrier flow or oil droplets in an aqueous flow) that are partitioned from each other and the fluid medium by the oil/water interface. This provides a method to retain the target molecules (analytes) within the magnetic trap for optical signal intensification even after the droplet which solvated the magnetic nanoparticles has passed from the zone. By employing enough magnetic field strength and adequately sized magnetic cores, the nanoparticles will be retained and will accumulate as droplet after droplet pass by and wash over them, releasing their nanoparticles into a growing fluorescent "cloud" at the optical detector.

In this magnetic emulsion particle capture system 300 the magnetic force will overcome both the Stoke's drag and the surface tension of the oil/water interface since the particles will pass though that interface. This effect, correctly applied, will provide the capability to increase the signal to noise or improve the instrument's limit of detection (LOD) proportional to the number of droplets that pass through the magnetic capture zone for optical interrogation. In this way 1000 droplets (approximately 1 second of droplet production for the author's microfluidic circuits) will increase the optical signal 3 orders of magnitude over any individual droplet. This effect will be useful in instruments that perform PCR, binding assays, chemical detection, and any other systems where near real-time performance or highly sensitive limits of detection are beneficial. This performance enhancement may provide the transformational impetus needed to move many biomedical instruments from the laboratory to point-of-care locations, and hence multiply the number of instruments needed. Similarly, the present invention will increase sensitivity and performance in slug flow systems (PCR by Quake and Thorsen) and continuous, non-segmented streams such as water quality monitoring MOEMS applications now becoming ubiquitous.

The system 300 will sequester the sample 304 and nanoparticles 304a close to the magnetic walls first, then as this region fills the center of the channel 302 (where the highest flow rates occur) will begin to accumulate them as well. Once the channel 302 has been saturated with the sample 304 and nanoparticles 304a, the optical density of fluorophores will be highest, at which time the instrument will be its most sensitive. Optical excitation by LED, laser, or other means 316 will elicit the strongest response, and the system will capture this signal at such sensors as a photodiode with trans-impedance amplifier, or an imaging array such as a CCD or CMOS imager 317.

This system 300 provides a method to uniquely deal with the radically different physics of the potential flow regimes at the microscale. For target molecule accumulation within the optical enhancement zone 312 of a continuous flow partitioned (emulsion) system, the magnetic force will be increased (by increasing B) to not only counter Stoke's drag, but also to counter the significant resistance of breaking the magnetic nanoparticles through the surface tension at the water/oil interface. Of considerable benefit is that oil, a non-polar and non-magnetic fluid, has a much lower volumetric magnetic susceptibility than does water, a polar solvent. For other flow regimes, slug, or continuous with only aqueous contents, a lower magnetic force will suffice. No matter which flow regime is being employed, the method allows for the electromagnet to be de-energized, allowing all captive particles to wash downstream. The empty droplets are discarded, freeing the channel 302 for the next experiment or measurement.

Referring again to FIG. 3, sample washing and reagent replacement or refresh can also be performed with this system 300. The target molecules, attached to the magnetic beads and held in the detection zone, can be washed by the continuous flow of the channel which, with upstream valving, can bring new and different reagents for multi-step reactions, or change the buffered pH to improve the optical efficiency of the fluorescing probe. For reagent sequencing, this method allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" by electromagnetic attraction. It should be noted that fluorescence requires an excitation source to raise electrons to their excited state which is why FIG. 3 includes laser or LED excitation.

The system 300 can perform in-line sample focusing of target analytes, whether in continuous flow, slug flow, or partitioned in emulsion microreactors, for subsequent optical detection at greatly reduced times compared to other methods. The system 300 can also perform in-line sample washing and buffering for complex reactions, and a real-time system for enhancing fluorescence detection through pH optimization.

Figure 4:
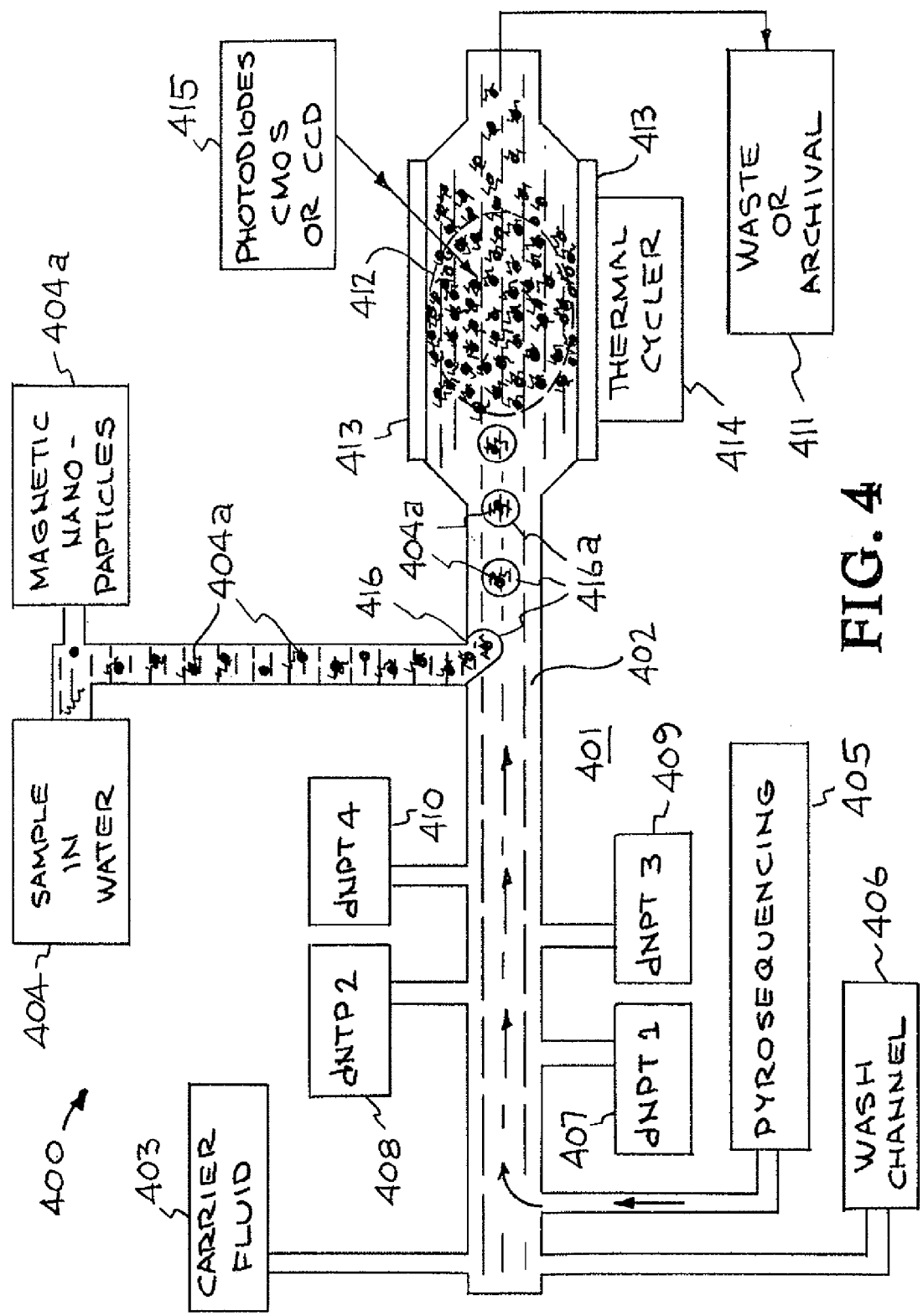
FIG. 4 illustrates yet another embodiment of a system for sequencing a nucleic acid constructed in accordance with the present invention.

Referring now to FIG. 4, a system for sequencing a nucleic acid constructed in accordance with the present invention is illustrated. The system is designated generally by the reference numeral 400. The system 400 provides pyrosequencing individual single or double stranded nucleic acids by isolating the nucleic acid, hybridizing the nucleic acid to magnetically-cored nanoparticles or to magnetic polystyrene-coated beads, positioning the nucleic acid in a magnetic trap, amplifying the nucleic acids, and sequencing the nucleic acid. The system 400 is capable of performing, singly or in combination, reagent and analyte mixing, cell-lysing, nucleic acid amplification, optical detection of amplification, reagent mixing for sequencing, optical detection of sequencing (which provides the exact sequence), and reagent wash to prevent cross contamination with the next analysis run.

The system 400 provides pyrosequencing a nucleic acid on a microchip 401. The microchip 401 includes a microchannel flow channel 402. A carrier fluid source 403 introduces a carrier fluid into the flow channel 402. The sample 404 to be analyzed together with suspended magnetic particles 404a is introduced to the flow channel 402 and droplets or microreactors containing the sample with magnetic particles 404a are formed. The flow channel 402 can carry genomic viral, bacterial, plant, animal, or human nucleic acid hybridized to magnetic-cored nanoparticles 404a (or polystyrene beads). The microchannel flow channel cross section aspect ratio, width and depth, is sized to prevent the magnetic nanoparticles or magnetic polystyrene-coated beads from vertical stacking.

A reagent source 405 introduces sequencing reagents into the flow channel 402. A wash solution source 406 allows a wash solution to be introduced into the flow channel 402 as needed. A first nucleotides (dNTP1) source 407 introduces dNTP1 nucleotides into the flow channel 402. A second nucleotides (dNTP2) source 408 introduces dNTP2 nucleotides into the flow channel 402. A third nucleotides (dNTP3) source 409 introduces dNTP3 nucleotides into the flow channel 402. A fourth nucleotides (dNTP4) source 410 introduces dNTP4 nucleotides into the flow channel 402.

A droplet maker 416 produces droplets or microreactors 416a. The droplets or microreactors 416a containing the sample 404 with magnetic particles 404a are carried to a PCR/sequencing zone 412 by the carrier fluid. The droplets or microreactors 416a containing the sample 404 with magnetic particles 404a are trapped in the PCR/sequencing zone 412 by activation of electromagnets 413. The drops (isolated mobile PCR reactors) 416a with their suspended magnetic particles are captured in the magnetic and fluidic trap (PCR/sequencing zone) 412 using the electro magnets 413. A thermalcycler 414 provides PCR and/or sequencing of the sample. A detector system 415 provides detection and sequencing of the sample.

When the droplets 416a pass through the optical enhancement, or "Capture Zone" 412, the electromagnets 413 strip the passing droplets of their nanoparticles, accumulating them first near the walls (close to the magnets) and then further and further into the free stream of the fluid flow. The detector system 415 provides pyrosequencing of the nucleic acids. As they fluoresce, their emission is read by a photodiode with amplification (such as a Trans-impedance amplifier), or an imaging system such as a CCD or CMOS array. After the measurement is taken, the magnets 413 are de-energized and the magnetic beads, or nanoparticles 404a, wash away, clearing the channel 402 for the next assay.

Referring again to FIG. 4, sample washing and reagent replacement or refresh can also be performed with this system 400. The target molecules, attached to the magnetic beads and held in the detection zone, can be washed by the continuous flow of the channel 402. For reagent sequencing, this method allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

The system 400 can perform in-line sample focusing of target analytes, whether in continuous flow, slug flow, or partitioned in emulsion microreactors, for subsequent optical detection at greatly reduced times compared to other methods. The system 400 can also perform in-line sample washing and buffering for complex reactions, and a real-time system for enhancing fluorescence detection through pH optimization.

Figure 5A:
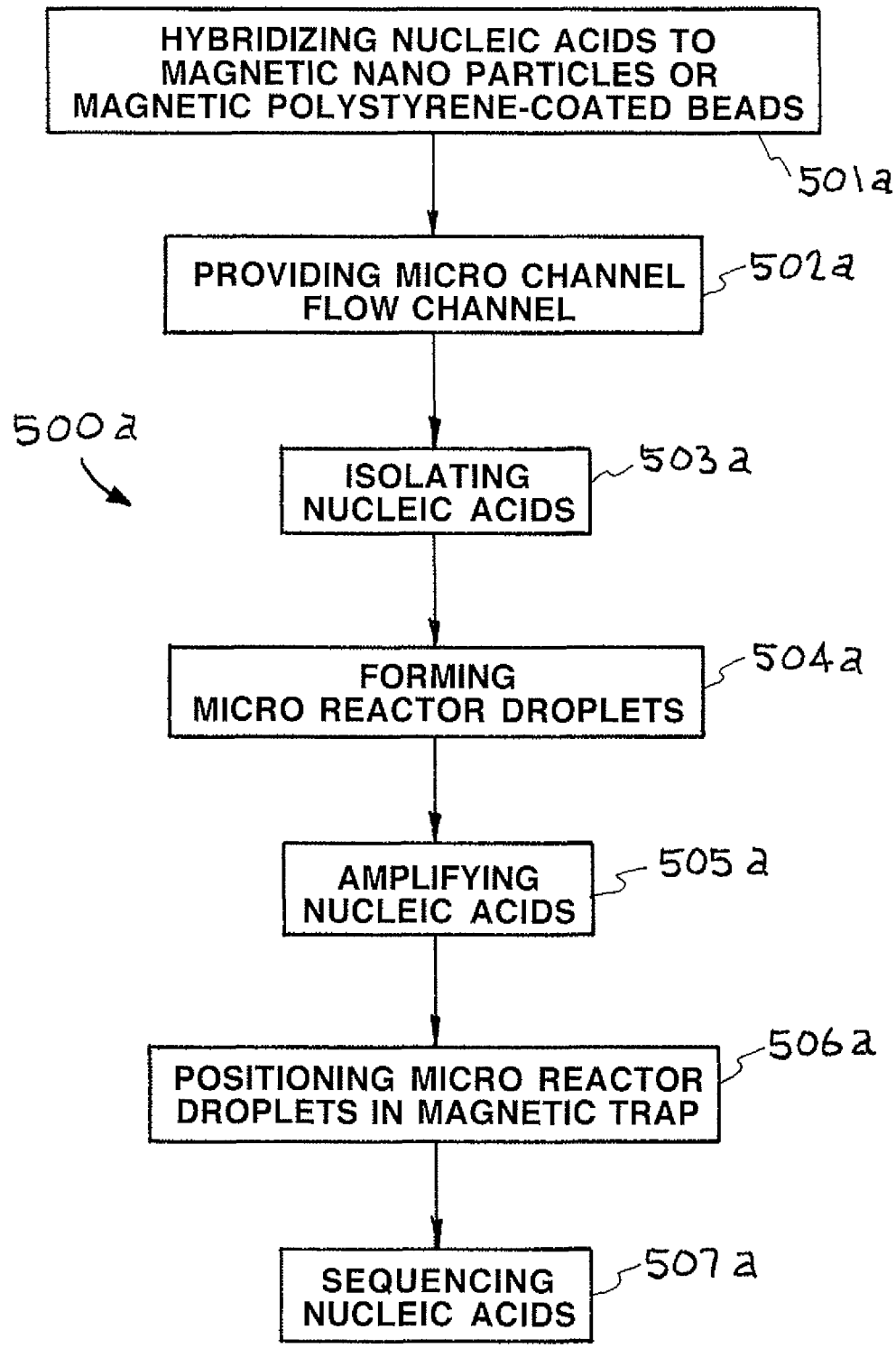
FIGS. 5A and 5B illustrate additional embodiments of methods of sequencing nucleic acids on a microchip.

Referring now to FIG. 5A, a method of sequencing nucleic acids on a microchip is illustrated. The method is designated generally by the reference numeral 500a. The system 500a provides sequencing individual single or double stranded nucleic acids by isolating the nucleic acid, hybridizing the nucleic acid to magnetically-cored nanoparticles or to magnetic polystyrene-coated beads, positioning the nucleic acid in a magnetic trap, and sequencing the nucleic acid. The system 500a is capable of performing, singly or in combination, reagent and analyte mixing, cell-lysing, nucleic acid amplification, optical detection of amplification, reagent mixing for sequencing, optical detection of sequencing (which provides the exact sequence), and reagent wash to prevent cross contamination with the next analysis run.

As illustrated in FIG. 5A, the method 500a includes the step 501a of hybridizing the nucleic acids to magnetic nanoparticles or to magnetic polystyrene-coated beads; the step 502b of providing a microchannel flow channel in the microchip; the step 503a of isolating the nucleic acids; the step 504a of forming microreactor droplets in the microchannel flow channel, the microreactor droplets containing the nucleic acids and the magnetic nanoparticles or magnetic polystyrene-coated beads; the step 505a of amplifying the nucleic acids; the step 506a of positioning the microreactor droplets containing the nucleic acids and the magnetic nanoparticles or magnetic polystyrene-coated beads in a magnetic trap in the microchannel flow channel; and the step 507a of sequencing the nucleic acids. The step 507a of sequencing of the nucleic acids can be various methods of sequencing of nucleic acids. For example the step 507a of sequencing the nucleic acids can be four-color sequencing by synthesis or pyrosequencing.

Figure 5B:
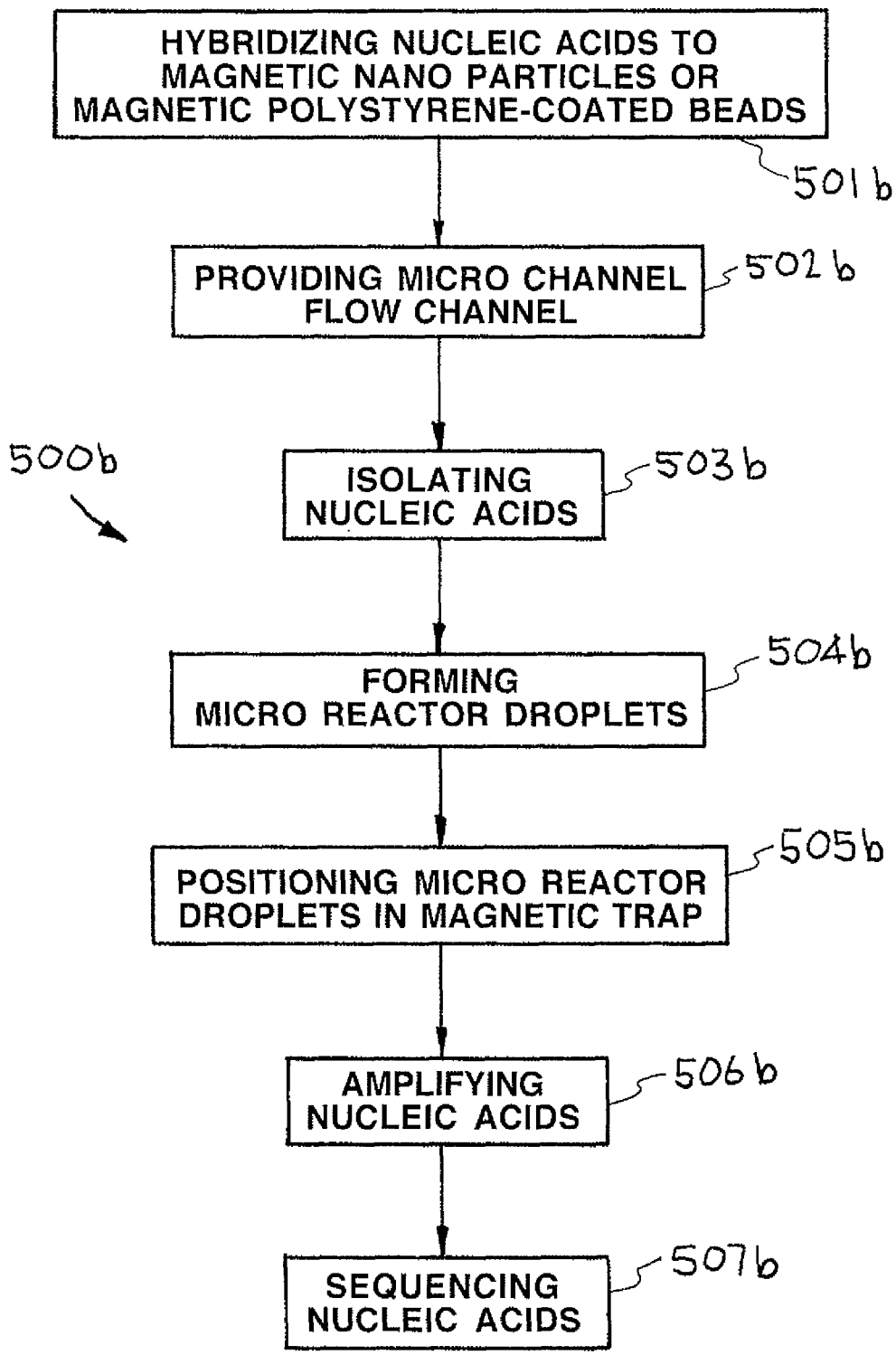

Referring now to FIG. 5B, a method of sequencing nucleic acids on a microchip is illustrated. The method is designated generally by the reference numeral 500b. The system 500b provides sequencing individual single or double stranded nucleic acids by isolating the nucleic acid, hybridizing the nucleic acid to magnetically-cored nanoparticles or to magnetic polystyrene-coated beads, positioning the nucleic acid in a magnetic trap, and sequencing the nucleic acid. The system 500b is capable of performing, singly or in combination, reagent and analyte mixing, cell-lysing, nucleic acid amplification, optical detection of amplification, reagent mixing for sequencing, optical detection of sequencing (which provides the exact sequence), and reagent wash to prevent cross contamination with the next analysis run.

As illustrated in FIG. 5B, the method 500b includes the step 501b of hybridizing the nucleic acids to magnetic nanoparticles or to magnetic polystyrene-coated beads; the step 502b of providing a microchannel flow channel in the microchip; the step 503b of isolating the nucleic acids; the step 504b of forming microreactor droplets in the microchannel flow channel, the microreactor droplets containing the nucleic acids and the magnetic nanoparticles or magnetic polystyrene-coated beads; the step 506b of positioning the microreactor droplets containing the nucleic acids and the magnetic nanoparticles or magnetic polystyrene-coated beads in a magnetic trap in the microchannel flow channel; the step 506b of amplifying the nucleic acids; and the step 507b of sequencing the nucleic acids. The step 507b of sequencing of the nucleic acids can be various methods of sequencing of nucleic acids. For example the step 507b of sequencing the nucleic acids can be four-color sequencing by synthesis or pyrosequencing.

The systems 500a and 500b employ magnetic beads or iron-cored nanoparticles coated with polystyrene. The magnetic beads have the ability to be coated, hybridized to, washed and removed in chemical reactions, to be captured within the optical focus, after the desired chemical reactions have occurred, within the microscale width of a MOEMS channel.

The magnetic nanoparticles are mixed with a nucleic acid sample and reagents and are formed into droplets by a droplet maker. The droplets flow through the systems 500a and 500b. The particles are coated through simple chemistry, with molecules that will bind with the chemical or biological molecule or complex that you wish to detect. The systems 500a and 500b pass the flow between electromagnets positioned above and below or on both sides of the channel to capture and highly concentrate the target molecules from the emulsion droplets, fluid slugs, or diluted stream. Whitesides et al. give the force developed in a magnetic trap by:

$$F = \frac{(\chi_p - \chi_m)V}{\mu_0}(B \cdot \nabla B) \qquad \text{[Equation 1]}$$

Where V is the particle volume, $\mu_0$ to is the magnetic permeability of free space, B is the magnetic field vector, and $(\chi_p - \chi_m)$ is the difference in the volumetric magnetic susceptibilities between the particle and the medium—in this case the flow medium (water, oil, gas, etc.)

To capture a particle and retain it in the optical intensity enhancement trap requires at a minimum the magnetic force overcoming the fluid drag force, which at the length scales of MOEMS circuits is governed by Stoke's flow. (Stoke's flow is a linearized solution of the Navier-Stokes equations which accounts for the insignificance of inertia affects to flow in micron-scale channels.)

$$F=6\pi\mu U_0 a \quad \text{[Equation 2]}$$

Where $\mu$ is the fluid media viscosity, $U_0$ is the mean flow rate, and a is the particle radius. For emulsions, this assumes an upstream microdroplet generator has been employed, such as a T-junction or constricted orifice, to create microdroplet reactors (aqeous droplets in an oil carrier flow or oil droplets in an aqeous flow) that are partitioned from each other and the fluid medium by the oil/water interface. This provides a method to retain the target molecules (analytes) within the magnetic trap for optical signal intensification even after the droplet which solvated the magnetic nanoparticles has passed from the zone. By employing enough magnetic field strength and adequately sized magnetic cores, the nanoparticles will be retained and will accumulate as droplet after droplet pass by and wash over them, releasing their nanoparticles into a growing fluorescent "cloud" at the optical detector.

In the magnetic emulsion particle capture systems 500a and 500b the magnetic force will overcome both the Stoke's drag and the surface tension of the oil/water interface since the particles will pass though that interface. This effect, correctly applied, will provide the capability to increase the signal to noise or improve the instrument's limit of detection (LOD) proportional to the number of droplets that pass through the magnetic capture zone for optical interrogation. In this way 1000 droplets (approximately 1 second of droplet production for the author's microfluidic circuits) will increase the optical signal 3 orders of magnitude over any individual droplet. This effect will be useful in instruments that perform PCR, binding assays, chemical detection, and any other systems where near real-time performance or highly sensitive limits of detection are beneficial. This performance enhancement may provide the transformational impetus needed to move many biomedical instruments from the laboratory to point-of-care locations, and hence multiply the number of instruments needed. Similarly, the present invention will increase sensitivity and performance in slug flow systems (PCR by Quake and Thorsen) and continuous, non-segmented streams such as water quality monitoring MOEMS applications now becoming ubiquitous.

The systems 500a and 500b will sequester nanoparticles close to the magnetic walls first, then as this region fills the center of the channel (where the highest flow rates occur) will begin to accumulate them as well. Once the channel has been saturated with nanoparticles, the optical density of fluorophores will be highest, at which time the instrument will be its most sensitive. Optical excitation by LED, laser, or other means will elicit the strongest response, and the system will capture this signal at such sensors as a photodiode with transimpedance amplifier, or an imaging array such as a CCD or CMOS imager.

The systems 500a and 500b provide a method to uniquely deal with the radically different physics of the potential flow regimes at the microscale. For target molecule accumulation within the optical enhancement zone of a continuous flow partitioned (emulsion) system, the magnetic force will be increased (by increasing B) to not only counter Stoke's drag, but also to counter the significant resistance of breaking the magnetic nanoparticles through the surface tension at the water/oil interface. Of considerable benefit is that oil, a non-polar and non-magnetic fluid, has a much lower volumetric magnetic susceptibility than does water, a polar solvent. For other flow regimes, slug, or continuous with only aqueous contents, a lower magnetic force will suffice. No matter which flow regime is being employed, the method allows for the electromagnet to be de-energized, allowing all captive particles to wash downstream. The empty droplets are discarded, freeing the channel for the next experiment or measurement.

The captured magnetic particles are retained in a PCR zone and PCR is powered by cyclic heating and cooling. The reactions between the hybridized molecules on the magnetic nanoparticle and the catalyzed and buffered reagents within the aqueous stream occur, powered by the addition of heat or light into the channel if necessary. When the droplets pass through the optical enhancement, or "Capture Zone," the electromagnets strip the passing droplets of their nanoparticles, accumulating them first near the walls (close to the magnets) and then further and further into the free stream of the fluid flow.

The flow channel, in addition to thermal control and detection elements, contains optical windows for delivering and detecting light. Following amplification the emulsions are broken, sequencing occurs as described above, and the dNTP's and sequencing reagents are sequentially washed over the captive particles. The imaging detector records particle location and intensity through each step of the process.

After the measurement is taken, the magnets are de-energized and the magnetic beads, or nanoparticles, wash away, clearing the channel for the next assay. Once complete the magnets are de-energized and the particles washed out to waste 411. Priming the channel with an aqueous wash refreshes it for the next sequencing experiment.

Referring again to FIG. 5, sample washing and reagent replacement or refresh can also be performed with the systems 500a and 500b. The target molecules, attached to the magnetic beads and held in the detection zone, can be washed by the continuous flow of the channel which, with upstream valving, can bring new and different reagents for multi-step reactions, or change the buffered pH to improve the optical efficiency of the fluorescing probe. For reagent sequencing, this method allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

The systems 500a and 500b provide a system for up to a thousand fold signal enhancement for optical detection of bacterial cells, virus particles, nucleic acids, proteins, biomolecules, chemical agents, explosives agents, and other targets of interest in a microfluidic (MOEMS) device. The systems 500a and 500b can perform in-line sample focusing of target analytes, whether in continuous flow, slug flow, or partitioned in emulsion microreactors, for subsequent optical detection at greatly reduced times compared to other methods. The systems 500a and 500b can also perform in-line sample washing and buffering for complex reactions, and a real-time system for enhancing fluorescence detection through pH optimization.

Figure 6:
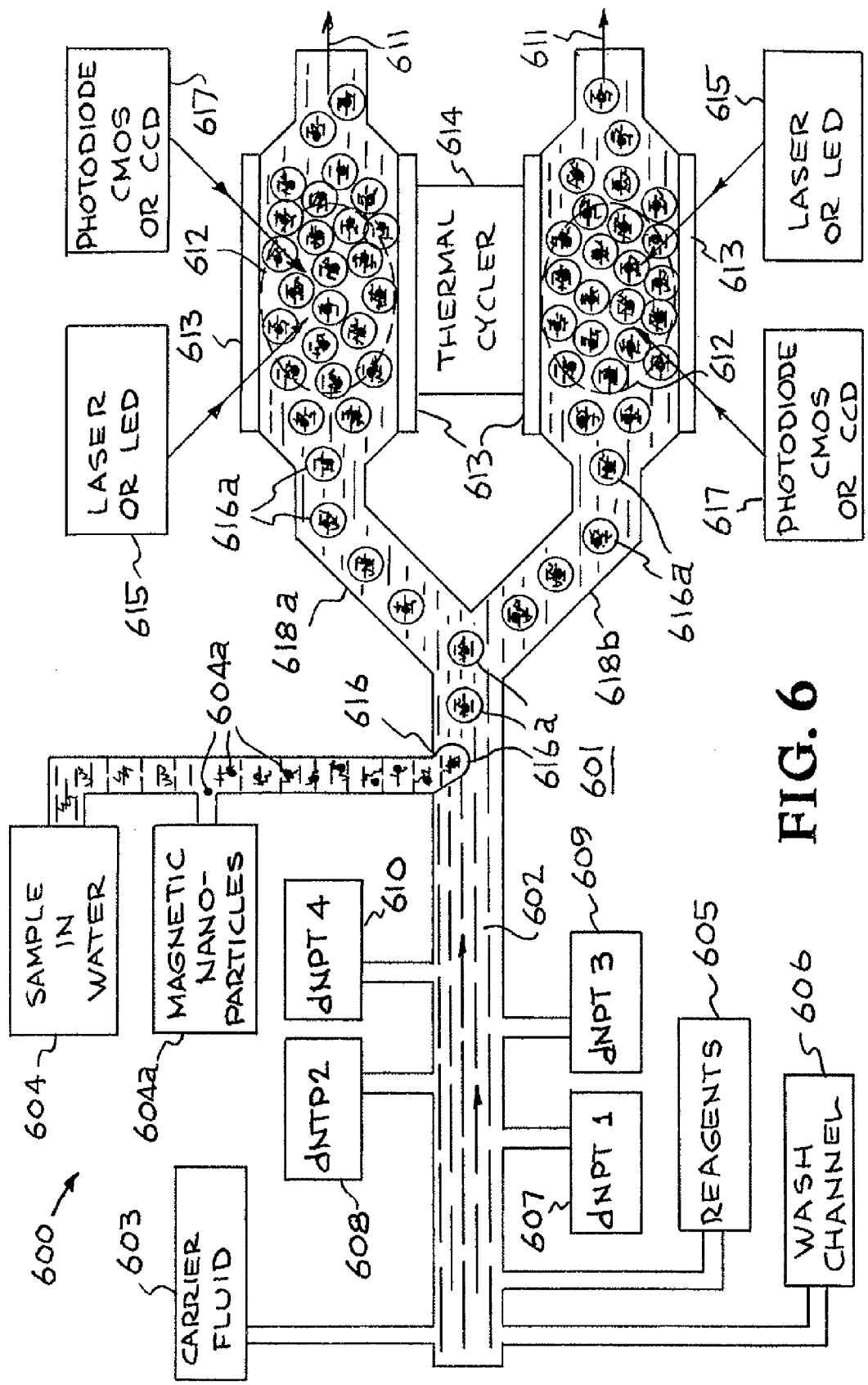
FIG. 6 illustrates a system for sequencing a nucleic acid having a microfluidic network of parallel or branched microchannels.

Referring now to FIG. 6, a system for sequencing a nucleic acid having a microfluidic network of parallel or branched microchannels constructed in accordance with the present invention is illustrated. The system is designated generally by the reference numeral 600. The system 600 provides sequencing individual single or double stranded nucleic acids by isolating the nucleic acid, hybridizing the nucleic acid to magnetically-cored nanoparticles or to magnetic polystyrene-coated beads, positioning the nucleic acid in a magnetic trap, and sequencing the nucleic acid. The system 600 is capable of performing, singly or in combination, reagent and analyte mixing, cell-lysing, nucleic acid amplification, optical detection of amplification, reagent mixing for sequencing, optical detection of sequencing (which provides the exact sequence), and reagent wash to prevent cross contamination with the next analysis run.

The system 600 provides sequencing a nucleic acid on a microchip 601. The microchip 601 includes a microchannel flow channel 602. A carrier fluid source 603 introduces a carrier fluid into the flow channel 602. The sample 604 to be analyzed together with suspended magnetic particles 604a is introduced to the flow channel 602 and droplets or microreactors containing the sample with magnetic particles 604a are formed. The flow channel 602 can carry genomic viral, bacterial, plant, animal, or human nucleic acid hybridized to magnetic-cored nanoparticles 604a (or polystyrene beads). The microchannel flow channel cross section aspect ratio, width and depth, is sized to prevent the magnetic nanoparticles or magnetic polystyrene-coated beads from vertical stacking.

A reagent source 605 introduces sequencing reagents into the flow channel 602. A wash solution source 606 allows a wash solution to be introduced into the flow channel 602 as needed. A first nucleotides (dNTP1) source 607 introduces dNTP1 nucleotides into the flow channel 602. A second nucleotides (dNTP2) source 608 introduces dNTP2 nucleotides into the flow channel 602. A third nucleotides (dNTP3) source 609 introduces dNTP3 nucleotides into the flow channel 602. A fourth nucleotides (dNTP4) source 610 introduces dNTP4 nucleotides into the flow channel 602.

A droplet maker 616 produces droplets or microreactors 616a. The droplets or microreactors 616a contain the sample 604 with magnetic particles 604a. The droplets or microreactors 616a are carried to a microfluidic network of parallel or branched microchannels 618a and 618b. The microfluidic network of parallel or branched microchannels 618a and 618b have a PCR/sequencing zone 612. The droplets or microreactors 616a containing the sample 604 with magnetic particles 604a are carried to a PCR/sequencing zone 612 by the carrier fluid. The drops (isolated mobile PCR reactors) 616a with their suspended magnetic particles are captured in the magnetic and fluidic trap (PCR/sequencing zone) 612 using electro magnets 613. A thermalcycler 614 provides PCR and/or sequencing of the sample. A detector system 615 and 617 provides detection and sequencing of the sample. The system can be exhausted to waste 611.

When the droplets 616a pass through the optical enhancement, or "Capture Zone" 612, the electromagnets 613 strip the passing droplets of their nanoparticles, accumulating them first near the walls (close to the magnets) and then further and further into the free stream of the fluid flow. The detector system 615 and 617 provides sequencing of the nucleic acids.

Figure 7:
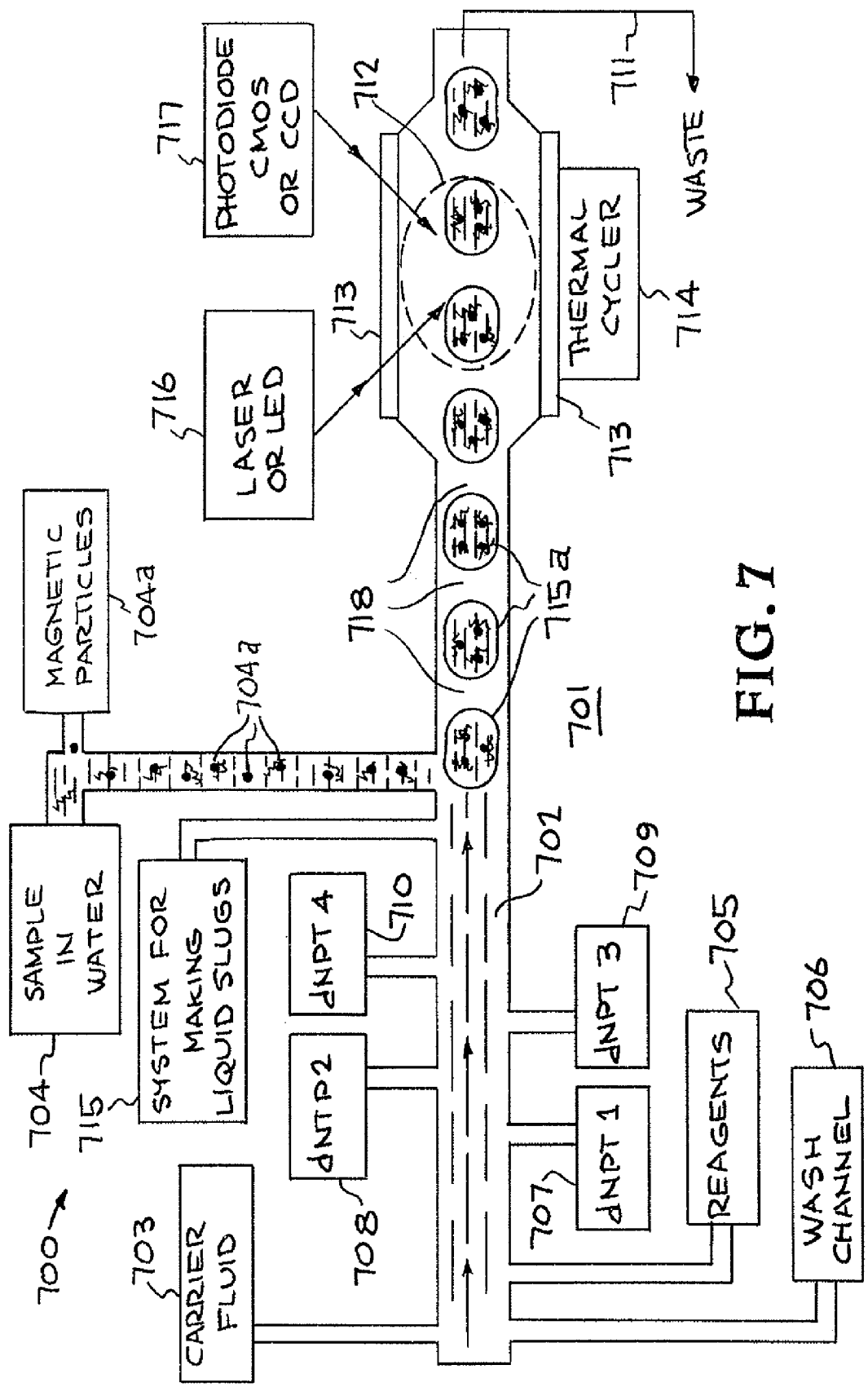
FIG. 7 illustrates yet another embodiment of a system for analysis of a nucleic acid constructed in accordance with the present invention.

Referring now to FIG. 7, yet another embodiment of a system for analysis of a nucleic acid constructed in accordance with the present invention is illustrated. The system is designated generally by the reference numeral 700. The system 700 provides analysis of a nucleic acid by isolating the nucleic acid, hybridizing the nucleic acid to magnetically-cored nanoparticles or to magnetic polystyrene-coated beads, positioning the nucleic acid in a magnetic trap, and sequencing the nucleic acid.

The system 700 provides sequencing a nucleic acid on a microchip 701. The microchip 701 includes a microchannel flow channel 702. The microchannel flow channel cross section aspect ratio, width and depth, is sized to prevent the magnetic nanoparticles or magnetic polystyrene-coated beads from vertical stacking. A carrier fluid source 703 introduces a carrier fluid into the flow channel 702.

The flow of carrier fluid 703 occurs in channel 702 is separated into liquid slugs 715a that are metered by air into air sections 718. The carrier fluid source 703 includes a system 715 for pulsing air into the carrier fluid 703 to form the liquid slugs 715. The sample 704 to be analyzed together with the associated magnetic particles 704a are carried to a capture zone 712 by the carrier fluid 703a. The sample 704 to be analyzed together with the associated magnetic particles 704a are trapped in the capture zone 712 by activation of electromagnets 713. The sample 704 to be analyzed together with the associated magnetic particles 704a are captured in the magnetic and fluidic trap (capture zone) 712 using the electro magnets 713.

The flow channel 702 can carry genomic viral, bacterial, plant, animal, or human nucleic acid hybridized to magnetic-cored nanoparticles 704a (or polystyrene beads). A reagent source 705 introduces reagents into the flow channel 702. A wash solution source 706 allows a wash solution to be introduced into the flow channel 702 as needed. Deoxyribonucleic acid (DNA) and ribonucleic acid (RNA) components are added to the flow channel 702. The four bases found in DNA are adenine (A), cytosine (C), guanine (G), and thymine (T). A first nucleotide (dNTP1) source 707 introduces dNTP1 nucleotides into the flow channel 702. A second nucleotide (dNTP2) source 708 introduces dNTP2 nucleotides into the flow channel 702. A third nucleotide (dNTP3) source 709 introduces dNTP3 nucleotides into the flow channel 702. A fourth nucleotide (dNTP4) source 710 introduces dNTP4 nucleotides into the flow channel 702.

The liquid slugs or microreactors 715a containing the sample 704 with magnetic particles 704a are carried to a PCR/sequencing zone 712 by the carrier fluid 703. The liquid slugs (isolated mobile PCR reactors) 715a with their suspended magnetic particles are captured in the magnetic and fluidic trap (PCR/sequencing zone) 712 using the electro magnets 713. A thermalcycler 714 provides PCR and/or sequencing of the sample. A detector system 716 and 717 provides detection and sequencing of the sample.

The systems 100, 200, 300, 400, 500, 600, and 700 provide unexpected and improved results. The article "On-Chip, Real-Time, Single-Copy Polymerase Chain Reaction in Picoliter Droplets," by N. Reginald Beer, Benjamin J. Hindson, Elizabeth K. Wheeler, Sara B. Hall, Klint A. Rose, Ian M. Kennedy, and Bill W. Colston; in *Analytical Chemistry*, Vol. 79, No. 22: Nov. 15, 2007 shows that some portions or all of the systems 100, 200, 300, 400, 500, 600, and 700 were tested and analyzed. The article "On-Chip, Real-Time, Single-Copy Polymerase Chain Reaction in Picoliter Droplets," by N. Reginald Beer, Benjamin J. Hindson, Elizabeth K. Wheeler, Sara B. Hall, Klint A. Rose, Ian M. Kennedy, and Bill W. Colston; in *Analytical Chemistry*, Vol. 79, No. 22: Nov. 15, 2007 is incorporated herein by this reference. The article "New system detects small samples for big gains" in NewsLine, Vol. 32, No. 39, Nov. 16, 2007, also shows that some portions or all of the systems 100, 200, 300, 400, 500, 600, and 700 were tested and analyzed. The article "New system detects small samples for big gains" in NewsLine, Vol. 32, No. 39, Nov. 16, 2007 is incorporated herein by this reference.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for sequencing nucleic acids in a sample, wherein the sample contains the nucleic acids; comprising:
   a microchip;
   a flow channel in said microchip;
   a source of emulsion carrier fluid connected to said flow channel producing an emulsion carrier fluid in said flow channel;
   a sample and fluid source that provides a source of the sample that contains the nucleic acids and a fluid;
   a sample and fluid channel connected to said sample and fluid source;
   a source of magnetic particles;
   a magnetic particles channel connected to said source of magnetic particles;
   a sample, fluid, and magnetic particles channel connected to said sample and fluid channel and to said magnetic particles channel;
   said sample, fluid, and magnetic particles channel connecting the sample containing the nucleic acids, said fluid, and said magnetic particles to said flow channel;
   an emulsion microreactor maker connected to said flow channel for producing microreactors containing the sample containing nucleic acids, said fluid, and said magnetic particles,
   said emulsion microreactor maker including said emulsion carrier fluid, the sample, said fluid, said magnetic particles, and a junction in said flow channel,
   wherein the sample, said fluid, and said magnetic particles are injected into said emulsion carrier fluid in said flow channel producing said microreactors containing the sample, said fluid, and said magnetic particles suspended in said emulsion carrier fluid;
   a reagent source connected to said flow channel;
   a nucleotides source connected to said flow channel for introducing NTP1 nucleotides, NTP2 nucleotides, NTP3 nucleotides, and NTP4 nucleotides into said flow channel;
   a PCR and sequencing zone in said flow channel;
   an electromagnet trap for selectively magnetically trapping the nucleic acids and said magnetic particles at said PCR and sequencing zone in said flow channel;
   thermalcycler connected to said PCR and sequencing zone in said flow channel; and
   a detector for detection and sequencing of the nucleic acids.

2. The apparatus for sequencing nucleic acid in a sample of claim 1 wherein said emulsion microreactor maker is a droplet maker for producing droplets that are microreactors containing the nucleic acids and said magnetic particles.

3. The apparatus for sequencing nucleic acid in a sample of claim 1 including magnetic nanoparticles or magnetic polystyrene-coated beads and wherein said flow channel in said microchip has a cross section aspect ratio, width and depth, that is sized to prevent said magnetic nanoparticles or magnetic polystyrene-coated beads from vertical stacking.

4. The apparatus for sequencing nucleic acid in a sample of claim 1 wherein said electromagnet trap is in a microfluidic network of parallel or branched microchannels.

5. The apparatus for sequencing nucleic acid in a sample of claim 1 wherein said source of emulsion carrier fluid is a source of oil emulsion carrier fluid connected to said flow channel.

6. The apparatus for sequencing nucleic acid in a sample of claim 1 wherein said source of emulsion carrier fluid is a source of an electrically insulating, stable fluorocarbon-based fluid emulsion carrier fluid consisting of perfluorohexane or tetradecafluorohexane connected to said flow channel.

7. The apparatus for sequencing nucleic acid in a sample of claim 1 wherein said magnetic particles are magnetic-cored optically discrete nanoparticles.

8. The apparatus for sequencing nucleic acid in a sample of claim 1 wherein said magnetic particles are magnetic polystyrene-coated beads.

9. The apparatus for sequencing nucleic acid in a sample of claim 1 wherein said thermalcycler includes a resistance heater.

10. The apparatus for sequencing nucleic acid in a sample of claim 1 wherein said thermalcycler includes a resistive tape heater.

11. The apparatus for sequencing nucleic acid in a sample of claim 1 wherein said thermalcycler includes a laser heater.

12. The apparatus for sequencing nucleic acid in a sample of claim 1 wherein said detector includes a photodiode.

13. The apparatus for sequencing nucleic acid in a sample of claim 1 wherein said detector includes a CCD or CMOS array.

14. The apparatus for sequencing nucleic acid in a sample of claim 1 wherein said detector includes a laser.

15. The apparatus for sequencing nucleic acid in a sample of claim 1 wherein said detector includes a LED light source.

16. The apparatus for sequencing nucleic acid in a sample of claim 1 including a cover on said microchip, said cover extending over said
   flow channel in said microchip;
   said PCR and sequencing zone in said flow channel;
   said electromagnet trap for selectively magnetically trapping the nucleic acids and said magnetic particles at said PCR and sequencing zone in said flow channel; and
   said thermalcycler connected to said PCR and sequencing zone in said flow channel.

17. An apparatus for sequencing nucleic acid in a sample wherein the sample contains the nucleic acids; comprising:
   a microchip;
   a flow channel in said microchip;
   a source of emulsion carrier fluid connected to said flow channel producing an emulsion carrier fluid in said flow channel;
   a sample and fluid source that provides a source of the sample that contains the nucleic acids and a fluid;
   a sample and fluid channel connected to said sample and fluid source;
   a source of magnetic particles;
   a magnetic particles channel connected to said source of magnetic particles;
   a sample, fluid, and magnetic particles channel connected to said sample and fluid channel and to said magnetic particles channel;
   said sample, fluid, and magnetic particles channel connecting the sample containing the nucleic acids, said fluid, and said magnetic particles to said flow channel;

an emulsion microreactor maker connected to said flow channel for producing microreactors containing the sample containing nucleic acids, said fluid, and said magnetic particles, said emulsion microreactor maker including said emulsion carrier fluid, the sample, said fluid, said magnetic particles, and a junction in said flow channel, wherein the sample, said fluid, and said magnetic particles are injected into said emulsion carrier fluid in said flow channel producing said microreactors containing the sample, said fluid, and said magnetic particles suspended in said emulsion carrier fluid;

a reagent source connected to said flow channel;

a first nucleotides dNTP1 source;

a first nucleotides dNTP1 channel connected to said first nucleotides dNTP1 source and said flow channel for introducing NTP1 nucleotides into said flow channel, a second nucleotides dNTP2 source;

a second nucleotides dNTP2 channel connected to said second nucleotides dNTP2 source and said flow channel for introducing NTP2 nucleotides into said flow channel, a third nucleotides dNTP3 source;

a third nucleotides dNTP3 channel connected to said third nucleotides dNTP3 source and said flow channel for introducing NTP3 nucleotides into said flow channel, a fourth nucleotides dNTP4 source;

a fourth nucleotides dNTP4 channel connected to said fourth nucleotides dNTP4 source and said flow channel for introducing NTP4 nucleotides into said flow channel, a PCR and sequencing zone in said flow channel;

an electromagnet trap for selectively magnetically trapping the nucleic acids and said magnetic particles at said PCR and sequencing zone in said flow channel;

thermalcycler connected to said PCR and sequencing zone in said flow channel; and a detector for detection and sequencing of the nucleic acids.

18. An apparatus for sequencing nucleic acids in a sample, wherein the sample contains the nucleic acids; comprising:
a microchip,
a flow channel in said microchip,
a source of emulsion carrier fluid connected to said flow channel producing an emulsion carrier fluid in said flow channel,
a sample and fluid source that provides a source of the sample that contains the nucleic acids and a fluid;
a sample and fluid channel connected to said sample and fluid source;
a source of magnetic particles;
a magnetic particles channel connected to said source of magnetic particles;
a sample, fluid, and magnetic particles channel connected to said sample and fluid channel and to said magnetic particles channel;
said sample, fluid, and magnetic particles channel connecting the sample containing the nucleic acids, said fluid, and said magnetic particles to said flow channel;
an emulsion droplet maker connected to said flow channel for producing droplets containing sample containing the nucleic acids, said fluid, and said magnetic particles,
said emulsion microreactor maker including said emulsion carrier fluid, the sample, said fluid, said magnetic particles, and a junction in said flow channel connecting said sample, fluid, and magnetic particles flow channel and said flow channel,
wherein the sample, said fluid, and said magnetic particles are injected into said emulsion carrier fluid in said flow channel producing said droplets containing the sample, said fluid, and said magnetic particles suspended in said emulsion carrier fluid;
a reagent source connected to said flow channel,
a first nucleotides dNTP 1 source connected to said flow channel for introducing NTP1 nucleotides into said flow channel,
a second nucleotides dNTP2 source connected to said flow channel for introducing NTP2 nucleotides into said flow channel,
a third nucleotides dNTP3 source connected to said flow channel for introducing NTP3 nucleotides into said flow channel,
a fourth nucleotides dNTP4 source connected to said flow channel for introducing NTP4 nucleotides into said flow channel,
a PCR and sequencing zone in said flow channel,
an electromagnet trap for selectively magnetically trapping the nucleic acids and said magnetic particles at said PCR and sequencing zone in said flow channel,
thermalcycler connected to said PCR and sequencing zone in said flow channel, and
a detector for detection and sequencing of the nucleic acids.

19. The apparatus for sequencing nucleic acid in a sample of claim 18 including a cover on said microchip, said cover extending over said flow channel in said microchip;
said PCR and sequencing zone in said flow channel;
said electromagnet trap for selectively magnetically trapping the nucleic acids and said magnetic particles at said PCR and sequencing zone in said flow channel; and
said thermalcycler connected to said PCR and sequencing zone in said flow channel.

20. The apparatus for sequencing nucleic acid in a sample of claim 19 wherein said cover includes at least one window for said detector for detection and sequencing of the nucleic acids.

* * * * *